United States Patent
Belman et al.

(10) Patent No.: US 11,439,387 B2
(45) Date of Patent: Sep. 13, 2022

(54) OFFSET JAW SUTURING DEVICE, SYSTEM, AND METHODS

(71) Applicant: BOSS INSTRUMENTS, LTD., INC., Gordonsville, VA (US)

(72) Inventors: Yuri Belman, Campbell, CA (US); Alexander Borisovich Zatyuryukin, Moscow (RU); Patricia A. Moore, Park City, UT (US)

(73) Assignee: Boss Instruments, Ltd., Inc., Gordonsville, VA (US)

(*) Notice: Subject to any disclaimer, the term of this patent is extended or adjusted under 35 U.S.C. 154(b) by 410 days.

(21) Appl. No.: 16/432,620

(22) Filed: Jun. 5, 2019

(65) Prior Publication Data
US 2019/0282228 A1   Sep. 19, 2019

Related U.S. Application Data

(63) Continuation of application No. 13/491,488, filed on Jun. 7, 2012.

(Continued)

(51) Int. Cl.
  *A61B 17/062* (2006.01)
  *A61B 17/00* (2006.01)

(52) U.S. Cl.
  CPC .... *A61B 17/062* (2013.01); *A61B 2017/0023* (2013.01); *A61B 2017/00473* (2013.01); *A61B 2017/00477* (2013.01)

(58) Field of Classification Search
  CPC ........ A61B 17/062; A61B 2017/00477; A61B 2017/0023; A61B 2017/00473
  See application file for complete search history.

(56) References Cited

U.S. PATENT DOCUMENTS

| | | |
|---|---|---|
| 2,601,564 A | 6/1952 | Smith |
| 3,709,226 A | 1/1973 | Santos |

(Continued)

FOREIGN PATENT DOCUMENTS

| | | |
|---|---|---|
| CN | 101083941 | 12/2007 |
| EP | 931510 | 7/1999 |

(Continued)

OTHER PUBLICATIONS

Autosuture—Advancing Possibilities in Surgery, downloaded from http://www.autosuture.com/autosuture, 1 page.

(Continued)

*Primary Examiner* — Jing Rui Ou
(74) *Attorney, Agent, or Firm* — Nixon & Vanderhye P.C.

(57) ABSTRACT

Improved medical suturing devices, systems, and methods for maintaining a position and orientation of a suture needle at a fixed location relative to a suturing device. An exemplary device include a clamp having opposing grasping surfaces for grasping the needle at a first location, and a needle contacting surface for contacting the needle at a second location, the second location a distance axially away from the first location so as to inhibit unintended movement of the needle relative to the device, which may include rotation of the needle about the first location and rotation of the needle about its axis. In many embodiments, the device includes a first and second clamp and a mechanism for alternating grasping of the needle between the first and second clamp. The device may also be incorporated into a single-clamp needle grasping device.

19 Claims, 20 Drawing Sheets

Related U.S. Application Data

(60) Provisional application No. 61/494,785, filed on Jun. 8, 2011.

(56) References Cited

U.S. PATENT DOCUMENTS

| | | |
|---|---|---|
| 3,827,277 A | 8/1974 | Weston |
| 3,946,740 A | 3/1976 | Bassett |
| 4,242,902 A | 1/1981 | Green |
| 4,308,663 A | 1/1982 | Ciaffone |
| 4,373,530 A | 2/1983 | Kilejian |
| 4,440,171 A | 4/1984 | Nomoto et al. |
| 4,605,002 A | 8/1986 | Rebuffat |
| 4,635,638 A | 1/1987 | Weintraub et al. |
| 5,100,421 A | 3/1992 | Christoudias |
| 5,234,443 A | 8/1993 | Phan et al. |
| 5,242,458 A | 9/1993 | Bendel et al. |
| 5,282,800 A | 2/1994 | Foshee et al. |
| 5,282,806 A | 2/1994 | Haber et al. |
| 5,336,230 A | 8/1994 | Leichtling et al. |
| 5,417,701 A * | 5/1995 | Holmes ............. A61B 17/0469 606/147 |
| 5,456,684 A | 10/1995 | Schmidt et al. |
| 5,569,271 A | 10/1996 | Hoel |
| 5,578,052 A | 11/1996 | Koros et al. |
| 5,601,575 A | 2/1997 | Measamer et al. |
| 5,603,723 A | 2/1997 | Aranyi et al. |
| 5,662,665 A | 9/1997 | Ludwick |
| 5,665,096 A | 9/1997 | Yoon |
| 5,718,714 A | 2/1998 | Livneh |
| 5,749,879 A | 5/1998 | Middleman et al. |
| 5,833,697 A | 11/1998 | Ludwick |
| 5,851,208 A | 12/1998 | Trott |
| 5,876,412 A | 3/1999 | Piraka |
| 5,897,563 A | 4/1999 | Yoon et al. |
| 5,908,429 A | 6/1999 | Yoon |
| 5,910,148 A | 6/1999 | Reimels et al. |
| 5,921,996 A | 7/1999 | Sherman |
| 5,938,668 A | 8/1999 | Scirica et al. |
| 5,951,575 A | 9/1999 | Bolduc et al. |
| 5,951,587 A | 9/1999 | Qureshi et al. |
| 5,954,731 A | 9/1999 | Yoon |
| 5,954,733 A | 9/1999 | Yoon |
| 5,957,937 A | 9/1999 | Yoon |
| 5,961,531 A | 10/1999 | Weber et al. |
| 5,984,932 A | 11/1999 | Yoon |
| 5,993,466 A | 11/1999 | Yoon |
| 5,993,467 A | 11/1999 | Yoon |
| 6,004,332 A | 12/1999 | Yoon et al. |
| 6,071,289 A | 6/2000 | Stefanchik et al. |
| 6,077,278 A | 6/2000 | Mayer |
| 6,077,290 A | 6/2000 | Marini |
| 6,086,601 A | 7/2000 | Yoon |
| 6,126,665 A | 10/2000 | Yoon |
| 6,132,441 A | 10/2000 | Grace |
| 6,146,392 A | 11/2000 | Smith |
| 6,159,224 A | 12/2000 | Yoon |
| 6,171,316 B1 | 1/2001 | Kovac et al. |
| 6,206,894 B1 | 3/2001 | Thompson et al. |
| 6,206,896 B1 | 3/2001 | Howell et al. |
| 6,206,903 B1 | 3/2001 | Ramans |
| 6,394,998 B1 | 5/2002 | Wallace et al. |
| 6,517,552 B1 | 2/2003 | Nord et al. |
| 6,527,786 B1 | 3/2003 | Davis et al. |
| 6,530,932 B1 | 3/2003 | Swayze et al. |
| 6,638,286 B1 | 10/2003 | Burbank et al. |
| 6,877,352 B1 | 4/2005 | Schlereth |
| 6,976,992 B2 * | 12/2005 | Sachatello ......... A61B 17/0467 606/205 |
| 7,001,400 B1 | 2/2006 | Modesitt et al. |
| 7,025,775 B2 | 4/2006 | Gadberry et al. |
| 7,101,363 B2 | 9/2006 | Nishizawa et al. |
| 7,185,597 B1 | 3/2007 | Phillips et al. |
| 7,338,504 B2 | 3/2008 | Gibbens et al. |
| 7,588,583 B2 | 9/2009 | Hamilton et al. |
| 7,799,028 B2 | 9/2010 | Schechter et al. |
| 7,842,028 B2 | 11/2010 | Lee |
| 7,842,045 B2 | 11/2010 | Vandenbroek |
| 7,998,149 B2 | 8/2011 | Hamilton et al. |
| 8,157,817 B2 | 4/2012 | Bonadio et al. |
| 8,252,007 B2 | 8/2012 | Hamilton et al. |
| 8,257,371 B2 | 9/2012 | Hamilton et al. |
| 8,317,805 B2 | 11/2012 | Hamilton et al. |
| 8,419,754 B2 | 4/2013 | Laby et al. |
| 8,603,113 B2 | 12/2013 | Hamilton et al. |
| 8,617,187 B2 | 12/2013 | Hamilton et al. |
| 2002/0077649 A1 | 6/2002 | Lasner |
| 2003/0028216 A1 | 2/2003 | Hanson |
| 2004/0111009 A1 | 6/2004 | Adams et al. |
| 2004/0230221 A1 | 11/2004 | Gadberry et al. |
| 2005/0043746 A1 | 2/2005 | Pollak et al. |
| 2006/0020272 A1 | 1/2006 | Gildenberg |
| 2006/0079914 A1 | 4/2006 | Modesitt et al. |
| 2006/0095074 A1 | 5/2006 | Lee et al. |
| 2006/0142785 A1 | 6/2006 | Modesitt et al. |
| 2006/0173469 A1 | 8/2006 | Klein et al. |
| 2006/0190035 A1 | 8/2006 | Hushka et al. |
| 2006/0212048 A1 | 9/2006 | Crainich |
| 2006/0271074 A1 | 11/2006 | Ewers et al. |
| 2006/0282094 A1 | 12/2006 | Stokes et al. |
| 2007/0060930 A1 | 3/2007 | Hamilton et al. |
| 2007/0060931 A1 | 3/2007 | Hamilton et al. |
| 2007/0167959 A1 | 7/2007 | Modesitt et al. |
| 2007/0179509 A1 | 8/2007 | Nagata et al. |
| 2008/0046003 A1 | 2/2008 | Renger et al. |
| 2008/0228204 A1 | 9/2008 | Hamilton et al. |
| 2008/0243147 A1 | 10/2008 | Hamilton et al. |
| 2009/0209998 A1 | 8/2009 | Widmann |
| 2009/0287226 A1 | 11/2009 | Gellman et al. |
| 2009/0292300 A1 | 11/2009 | Hamilton et al. |
| 2010/0268257 A1 * | 10/2010 | Hamilton ........... A61B 17/0469 606/148 |
| 2011/0301605 A1 | 12/2011 | Horner |
| 2012/0010622 A1 | 1/2012 | Heinemann |
| 2012/0130404 A1 | 5/2012 | Meade et al. |
| 2012/0150199 A1 | 6/2012 | Woodward et al. |
| 2012/0165837 A1 | 6/2012 | Belman et al. |
| 2012/0271347 A1 | 10/2012 | Kaercher et al. |
| 2012/0283755 A1 | 11/2012 | Gellman et al. |
| 2013/0060262 A1 | 3/2013 | Hamilton et al. |
| 2014/0222036 A1 | 8/2014 | Hamilton et al. |
| 2014/0288581 A1 | 9/2014 | Hamilton et al. |
| 2015/0127025 A1 | 5/2015 | Hamilton et al. |
| 2015/0190132 A1 | 7/2015 | Hamilton et al. |
| 2016/0030036 A1 | 2/2016 | Belman et al. |

FOREIGN PATENT DOCUMENTS

| | | |
|---|---|---|
| EP | 1862125 | 12/2007 |
| EP | 2120728 | 8/2016 |
| JP | 2009514562 | 4/2009 |
| JP | 2013529981 | 7/2013 |
| WO | 1999/055217 | 11/1999 |
| WO | 1999/055237 | 11/1999 |
| WO | 2004/006780 | 1/2004 |
| WO | 2006/012128 | 2/2006 |
| WO | 2006/023348 | 3/2006 |
| WO | 2006/125835 | 11/2006 |
| WO | 2007/033314 | 3/2007 |
| WO | 2007/037326 | 4/2007 |
| WO | 2007/089603 | 8/2007 |
| WO | 2007/129121 | 11/2007 |
| WO | 2007/135629 | 11/2007 |
| WO | 2008/113076 | 9/2008 |
| WO | 2008/113080 | 9/2008 |
| WO | 2011/163634 | 12/2011 |
| WO | 2014/164890 | 10/2014 |

OTHER PUBLICATIONS

Endo Stitch 10 mm Suturing Device Instructions for Use and Product Description, United States Surgical, Tyco Healthcare Group LP, downloaded from the internet, 4 pages.

(56) References Cited

OTHER PUBLICATIONS

Fastclose Device Instructions for Use, SuturTek, Inc. product brochure, 2 pages.
Home Page for Auto Suture, United States Surgical, Tyco Healthcare Group LP product brochure, downloaded from the internet, 1 page.
Quik-Stitch Endoscopic Suturing System, downloaded from http://paresurgical.com, 1 page.
SuturTek—SuturTek Products—FastClose Device, SuturTek, Inc. product brochure, downloaded from the internet, 2 pages.
SuturTek—SuturTek Products—The Technology , SuturTek, Inc. product brochure, downloaded from the internet, 1 page.
"SuturTek—SuturTek Products—FastClose in Use," SuturTek, Inc. product brochure, downloaded from the internet, 1 page.
"The Running Device—Surgery's Best Suturing Technology ," downloaded from http://www.isisolutions.com/home.html, 1 page.
Australian Examination Report dated Dec. 11, 2015 in AU 2011270654.
Australian Examination Report dated Jan. 6, 2016 in AU 2012267865.
Australian Search Report dated Jan. 25, 2012 in AU 2006290868.
Canadian Office Action dated Aug. 31, 2016 in CA 2,906,901.
Canadian Office Action dated Feb. 23, 2017 in CA 2803278.
Canadian Office Action dated Mar. 14, 2013 in CA 2622405.
European Search Report and Supplementary Search Report dated May 31, 2017 in EP 11799021.8.
European Search Report dated Aug. 19, 2009 in EP 06803567.4.
European Search Report dated May 14, 2014 in EP 11192491.6.
European Search Report for PCT/US2012/041362, European Patent Office, dated Feb. 13, 2015.
International Search Report and Written Opinion for PCT Application No. PCT/US2008/057252 dated Aug. 15, 2008.
International Search Report and Written Opinion for PCT Application No. PCT/US2008/057260 dated Sep. 5, 2008.
International Search Report and Written Opinion for PCT Application No. PCT/US2010/020542 dated Mar. 2, 2010.
International Search Report and Written Opinion for PCT Application No. PCT/US2011/041902 dated Oct. 28, 2011.
International Search Report and Written Opinion for PCT Application No. PCT/US2013/053192 dated Nov. 29, 2013.
International Search Report and Written Opinion for PCT Application No. PCT/US2014/023711 dated Jul. 30, 2014.

* cited by examiner

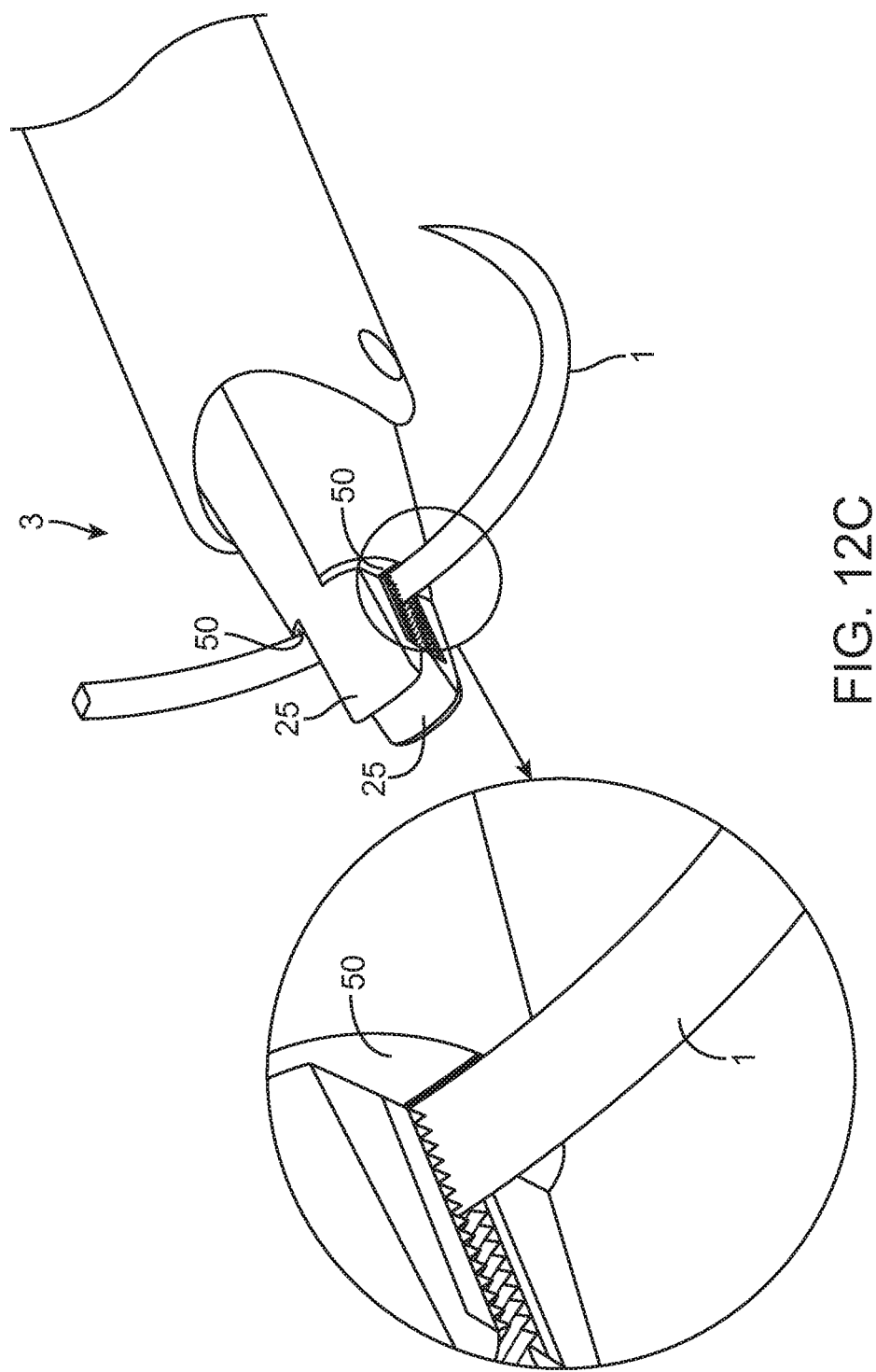

OFFSET JAW SUTURING DEVICE, SYSTEM, AND METHODS

CROSS-REFERENCE TO RELATED APPLICATIONS

This application is a continuation of U.S. application Ser. No. 13/491,488 filed Jun. 7, 2012, which designated the U.S. and claims priority to U.S. Provisional Application No. 61/494,785 filed Jun. 8, 2011, the entire contents of each of which are hereby incorporated by reference.

This application is generally related to U.S. Pat. No. 7,588,583 issued on Sep. 15, 2009; U.S. patent application Ser. No. 11/532,032 filed Sep. 14, 2006; U.S. patent application Ser. No. 12/535,499 filed Aug. 4, 2009; U.S. patent application Ser. No. 12/049,552 filed on Mar. 17, 2008; U.S. patent application Ser. No. 12/049,545 filed on Mar. 17, 2008; U.S. patent application Ser. No. 12/687,349 filed on Jan. 14, 2010; and U.S. Patent Application 61/358,764 filed on Jun. 25, 2010, the full disclosures of which are incorporated herein by reference.

BACKGROUND OF THE INVENTION

The present invention generally relates to medical devices, systems, and methods. In specific embodiments, the invention provides devices, systems, and methods for suturing tissues in open surgery, minimally invasive surgical procedures, and the like.

Although many aspects of surgery have changed radically over the last several decades, some surgical techniques have remained remarkably constant. For example, as was true fifty years ago, suturing remains a common technique for approximation of tissues, ligation of tissues, affixing tissues together, and the like.

Suture has been used in open surgical procedures for generations to therapeutically treat diseased tissue and to close surgical access sites and other wounds. More recently, the use of minimally invasive surgical techniques has expanded, with surgical therapies often being performed at internal surgical sites. Although a wide variety of visualization techniques (including laparoscopes and other endoscopic viewing devices, fluoroscopy and other remote imaging modalities, and the like) have been developed to allow surgeons to view these internal surgical sites, and although a large variety of new tissue treatment techniques have been developed (including ultrasound techniques, electrosurgical techniques, cryosurgical techniques, and the like) and are now widely available, many modern surgical interventions continue to rely on suturing.

A wide variety of alternatives to suturing of tissues have been developed, and have gained varying degrees of acceptance in certain surgical procedures. Staples and tissue adhesives are used quite frequently in many open and minimally invasive surgical settings, and a variety of tissue welding techniques have also been proposed. Nonetheless, suturing remains ubiquitous in surgery, as suturing provides a number of advantages over many of the alternatives.

Suture's advantages include the large knowledge and skill base that surgeons have developed over the years. Additionally, a variety of off-the-shelf, pre-packaged surgical needles with suture are available from a large number of suppliers at very reasonable cost. Surgeons are able to precisely control the location of suture stitches by grasping the suture needle and first pushing it and then pulling it through the target tissue. In open surgery the surgeon may manually grasp the suture needle directly with his or her hand, although both open and minimally invasive procedures are often performed by grasping the needle with a needle grasping tool, such as a needle holder, and manipulating the tool to place the suture stitches. The results obtained using suture are highly predictable, although dependent on the skill of the surgeon. In light of its advantages, the use of suture does not appear likely to disappear any time soon, with even modern robotic surgical techniques often making use of suture.

Although suture remains popular in surgery at least in part due to its significant advantages, suturing is not without disadvantages. In particular, when suturing with a needle grasping tool, such as a needle holder, the needle may have a tendency to slip or pivot about the point at which the needle is grasped. When suturing, it can be difficult to position a needle in precise alignment within the grasping tool, and even more difficult to maintain that alignment as the needle is subjected to various external forces during suturing. For example, during a typical suturing process, the needle is pushed with sufficient force to penetrate the tissue and then used to pull the suture through the tissue. After pulling a suture through the tissue, the needle is typically pulled taught to tighten the suture. The forces exerted on the needle by the tissue during penetration and the forces from the suture as it is pulled taught may cause misalignment of the needle within the tissue grasping tool. This misalignment may interfere with the suturing process, which may be delayed as the physician realigns the needle with the needle grasping tool. Another problem, is that when a needle become misaligned some physicians have a tendency to grab the needle with their hand to realign the needle, which can potentially lead to unnecessary contamination of tissues in the surgical environment and/or risks of the needle perforating through the glove and skin of the physician. Moreover, realignment of the needle once misaligned is even more difficult in a minimally invasive environment where the surgeon typically relies on an endoscope or imaging procedures to correct needle alignment. These difficulties may lead to increased fatigue for the physician and unnecessarily prolong surgery resulting in longer recovery periods for the patient. It would be desirable, therefore, for a needle grasping tool that allows for more accurate positioning and alignment of the needle with the tool, and for more stability in needle position and alignment during the suturing procedure.

Placing a large number of suture stitches can also be tiring and quite time-consuming. Manipulation of a suture needle can be difficult even in open surgery due to the limited space that is often available around the target tissues. The challenges of manipulating suture needles may be even greater in minimally invasive surgical procedures, where the needles are often manipulated using long-handled tools extending through a small aperture, typically while viewing the procedure on a display which is offset from the surgical site. Tools used in minimally invasive procedures are generally designed with reduced profiles to facilitate insertion of the tool through a minimally invasive aperture and to prevent tissue damage from movement of the tool in a minimally invasive environment. Tying knots with a desired amount of tension and the like may call for intricate and precise manipulation of the suture, further complicating and delaying open and minimally-invasive surgeries. In fact, the time spent closing/suturing the access site may be significantly greater than the time spent treating the underlying target tissues for many procedures.

There have been a variety of proposals for modifications to standard surgical suturing structures and methods to try to address the above disadvantages. At least some of these proposals may seek to rely on specialized and/or proprietary suturing needle systems, which could increase costs and preclude their wide acceptance, especially in third world countries. Unfortunately, many proposals for modifying existing suturing techniques may also decrease the surgeon's control over the placement of the suture, such as by relying on an automated or indirect mechanical movement of a device to drive a suture needle into and/or through tissues. While these new proposals have in the past or may in the future gain varying degrees of acceptance in one or more surgical procedures, standard suturing techniques continue to predominate throughout surgery in general.

In light of the above, it would be desirable to provide improved suturing devices, systems, and methods. It would be generally desirable to maintain some, most, or all of the advantages of standard suturing techniques, preferably while decreasing the time required for suturing, the strain on the surgeon, the training involved in achieving competence or time-efficiency in suturing techniques, or the like. It would be particularly advantageous if these improvements could be provided without requiring extensive capital investments for new equipment, without significant increases in complexity of the suturing process, or without having to resort to specialized or proprietary suturing needles and the like. Alternative needle grasper structures which improve the stability of needle position and alignment increase the ease and accuracy of stitching, and/or which are readily adapted for a variety of different procedures and patient physiologies would also be desirable.

BRIEF SUMMARY OF THE INVENTION

The present invention generally provides improved medical suturing devices, systems, and methods. Embodiments of the invention provide improved suturing devices and methods that maintain some or all of the advantages of standard open and/or minimally invasive suturing techniques while providing enhanced stability in needle position and alignment, thereby increasing speed and ease of use. Exemplary suturing devices may hold a suture needle at a first location between opposing grasping surfaces of a first clamp, while contacting the needle at a second location on the needle, the second location axially offset from the first location so as to inhibit unintended movement of the needle relative to the clamp when advancing the needle through the tissue, pulling a suture, and/or the like. In many embodiments, the needle contacting surface comprises a flat surface, often an offset portion of the clamp, typically an offset portion of a jaw of the clamp at a relatively fixed position in relation to the needle axes. The clamp may include a needle contacting surface extending laterally outward from one or both sides of the clamp so as to contact the needle a distance axially offset on either or on both sides of the first location of the needle grasped within the clamp. The needle contacting surface may act as a guide to help align an axis of the needle relative to the clamp before use, to facilitate verification that the needle remains aligned with the clamp during use, and/or as a support surface to inhibit movement of the needle from alignment with the clamp despite significant stresses and torque imposed on the needle during suturing, often without significantly altering the clamping loads between the opposing surfaces of the clamp and the needle. Hence, the simple laterally extending needle contacting surfaces(s) can provide surprisingly significant benefits to needle stability during a variety of suturing procedures.

In a first aspect, the suturing device comprises a first clamp having first and second opposed surfaces and a needle contacting surface. The opposing surfaces of the clamp generally have a closed configuration for grasping the needle at a first location and an open configuration for receiving or releasing the needle from between the opposing surfaces. In an exemplary embodiment, the opposing surfaces comprises inside surfaces of a pair of jaws of the clamp. The needle contacting surface is axially offset from the opposing surfaces so as to contact the needle at a second location, the second location being axially offset from the first location so as to inhibit unintended movement of the needle. The device further comprises an actuation mechanism for moving the opposing grasping surfaces toward each other so as to grasp the needle at the first location. In one embodiment, the actuation mechanism may comprise pivoting members having proximal handles, such as in a needle holder. In another embodiment, the actuation mechanism may comprise shafts operatively coupled to handles such that actuation of the handles cycles the mechanism so as to alternate between grasping with a first clamp and grasping with a second clamp, wherein one or both of the first and second clamps include a needle contacting surface for contacting the needle at the second location so as to inhibit unintended movement of the needle relative to the device.

In another aspect, the opposing surfaces of the clamp are substantially parallel when in the closed position. The needle comprises a needle axis extending through a plane of the needle, such as a curved needle extending through the plane of curvature of the needle. In many embodiments, the needle contacting surface is transverse to the plane of opposing surfaces, preferably substantially parallel to the plane along which each of the opposing surfaces extends, so that the rotation and movement of the needle about the first location at which the needle is grasped is constrained. In an exemplary embodiment, the needle contacting surface is flat, the plane of the surface being parallel to the plane of curvature when a curved needle is used, such that the contact between the flat needle contacting surface and the needle substantially constrains the needle to inhibit rotation of the needle about its axis.

In many embodiments, the clamp comprises a first and second jaw, wherein the opposing surfaces comprise the inside facing surfaces of the first and second jaws. In many embodiments, the needle contacting surface is formed from the first or second jaw, preferably in each of the first and second jaws. In many embodiments, each of the first and second jaws of a clamp include an offset defining a needle contacting surface, typically the offset of one jaw extending in one axial direction, while the offset of the other jaw extends in the opposite axial direction of the needle.

In one aspect, the opposing surfaces of the clamp may include grasping surfaces having a texture suited for grasping the needle. The grasping surface may comprise ridges, scoring, markings, indentions, or any suitable feature for improved grasping of the needle. In some embodiments, the grasping surface comprises a plurality of ridges or grooves that extend along the axial direction of the needle so as to receive at least a portion of the needle in the ridge or groove. In a preferred embodiment, the plurality of ridges comprise a series of triangular ridges extending along an axial direction of the needle when grasped between opposing surfaces of the clamp. The triangular ridges are typically dimensioned so as to fittingly receive an apex of a triangular cross-section of the needle so as to inhibit rotational movement of the needle along its axis when grasped between opposing surfaces, at least one of which comprises a grasping surface having a series of triangular ridges.

In many embodiments, the clamp may be included in a suturing device having one clamp, such as a needle holder, or a suturing device having multiple clamps, such as a suturing device having alternating clamps that cycle between grasping a proximal portion of the needle and a distal portion of the needle. A suturing device having relative to a handle of the device, allowing the surgeon to grasp and manipulate the handle so as to insert the needle through the tissues to be sutured in a manner closely analogous to use of a standard needle gripper. Cycling of the handle of the device from a closed position to an open position and back to the closed position may result in the needle being alternatingly gripped by a first clamp (for example, along a proximal portion of the needle, suitable for insertion of the tip of the needle into and through tissue), and then by a second clamp (for example, along a distal portion of the needle, suitable for pulling the protruding needle out from the tissue), and optionally again by the first clamp (ready for initiation of the next stitch). The needle will often remain at a substantially fixed location relative to the body and handle of the suturing device during at least the insertion and/or pulling of the needle through the tissue, allowing the surgeon to maintain precise control over needle movement and positioning of the suture. Advantageously, standard off-the-shelf suturing needles with their attached suture may be used, and the device may be employed in an open surgical setting or a minimally invasive procedure.

In another aspect, the invention provides suturing methods. The suturing method comprises grasping a first location of a suturing needle between first and second opposing grasping surfaces of a first clamp of a suturing device, contacting the needle at a second location with a needle contacting surface of the first clamp, and advancing the needle within the tissue with the suturing device while grasping the suturing needle between the opposing surfaces and while contacting the needle at the second location, the second location axially offset axially along the needle from the first location so as to inhibit unintended movement of the needle relative to the clamp when advancing the needle. Typically, advancing the needle comprises inserting a distal portion of the suturing needle distally through the tissue by moving a proximal body of the suturing device. Ideally, the needle contacting surface contacts the needle at the second location concurrently with grasping of the needle at the first location so as to position the needle in a pre-determined alignment relative to the clamp during grasping of the needle. In one aspect, the opposing surfaces are sufficiently parallel so as to grasp the needle therebetween when the needle is separated from the needle contacting surface, and the method may further comprising determining that the needle is not in a desired alignment relative to the clamp by visually identifying a separation between the needle contacting surface and the needle while the clamp grasps the needle, and in response, repositioning the needle relative to the clamp.

In another embodiment, the method further includes countering a tissue torque exerted on the needle by the tissue about the first location when the distal portion of the needle is inserted through the tissue with a force exerted on the needle by the needle contacting surface of the clamp. The needle contacting surface may contact the needle on either on either side of the first location on the needle, although preferably the needle contacting surface contacts the needle on both sides of the first location on the needle. In many embodiments, the needle contacting surface extends axially away from the opposing grasping surface by an axial distance of at least ⅛$^{th}$ the width of the opposing surface along an axis of the needle, preferably at least half the width, and even more preferably between half and twice the width.

In another embodiment, the method further comprises grasping the distal portion of the needle inserted through the tissue at a first location between first and second opposing grasping surfaces of a second clamp, contacting the distal portion needle at a second location with a needle contacting surface of the second clamp. The method typically includes releasing the needle from the first clamp and axially moving the first clamp away from the needle. Generally, the physician pulls the proximal portion of the needle through the tissue by moving the second clamp away from the tissue while grasping the suturing needle between the opposing surfaces of the second clamp and while contacting the needle at the second location with the needle contacting surface of the clamp grasping the needle. The physician may then move the clamp to pull the suture taught, typically by moving a body of the device.

In another aspect, the method includes contacting a suturing needle at a first location along a plane of curvature of the needle with a needle contacting surface of a first clamp of a suturing device so as to position an axis of the needle at a desired alignment relative to the first clamp. The physician may the grasp a second location of the needle along a plane transverse to the plane of curvature of the needle between first and second opposing surfaces of the first clamp while the contacting surface of the first clamp contacts the first location. The physician then may advance the needle within the tissue while grasping the needle between the opposing surfaces and while contacting the needle at the second location the second location at least partly axially offset from the first location so as to inhibit unintended movement of the needle relative to the clamp.

BRIEF DESCRIPTION OF THE DRAWINGS

FIGS. 12A-12C are perspective views of the exemplary clamp of FIG. 10 grasping a needle.

DETAILED DESCRIPTION OF THE INVENTION

Figure 1A:
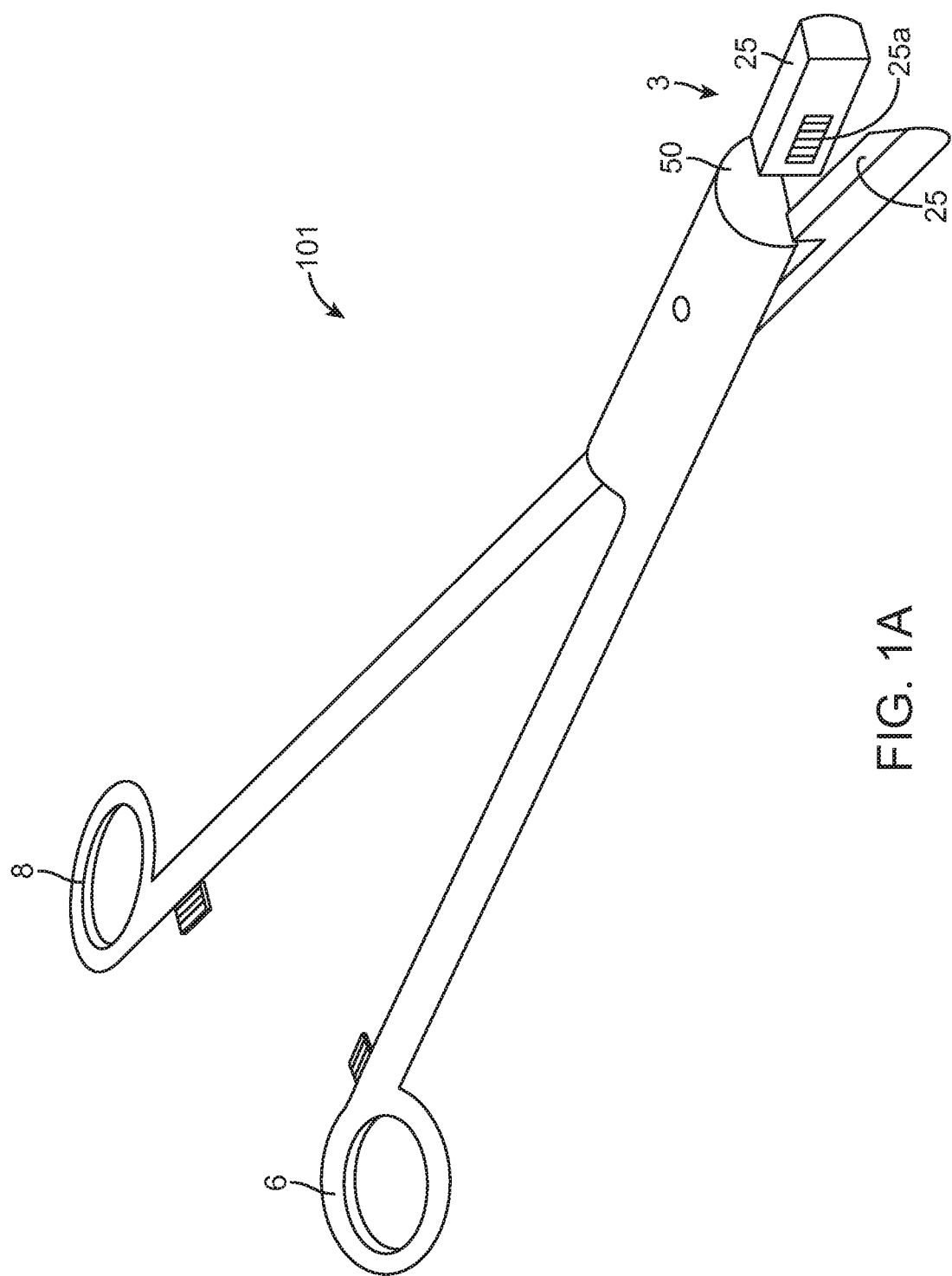
FIG. 1A is a perspective view of an exemplary suturing device with one jaw of the clamp having an offset portion defining a needle contacting surface, in accordance with many embodiments.

The present invention is generally directed to improved medical suturing devices, systems, and methods. Exemplary embodiments of the invention provide improved suturing devices and methods for suturing tissues that can significantly improve the positioning and alignment of a needle held in a suturing device, particularly useful when suturing of long incisions or where large numbers of stitches are to be deployed.

The invention should find a wide variety of applications for stitching anatomical tissues in both humans and animals. Along with endoscopic operations (for example, in laparoscopy) these structures and methods may find use in other areas of surgery where tissues are to be stitched, providing particular advantages for stitching of large incisions by increasing the ease and speed with which each individual stitch may be placed, as well as facilitating and expediting the formation of knots in the suture. The suturing devices and associated methods described herein may, for example, be used suture a wide variety of strata of anatomical tissues, including (but not limited to) subcutaneous layers, fascia, the outer skin, various organs (including the uterus), and the like. While exemplary embodiments are set forth below, these suturing devices and methods may be applicable to a wide variety of suturing operations, including open surgery, large and small cavity procedures, endoscopic procedures, microsurgeries (including for suturing of veins, arteries, and the like), and many specialized surgeries. Embodiments of these devices and methods may be particularly useful in surgeries involving long incisions, including plastic surgeries. A wide variety of blood vessels, including both veins and arteries, may also be stitched using the techniques described herein, for formation of anastomoses and the like. Along with increasing the stability of the needle's position and orientation in the suturing device, the invention also improves the speed and/or ease of forming surgical suture stitches and often allow the doctor to maintain control over the placement of the sutures by maintaining a fixed relationship between the movements of the doctor's hand and the insertion and withdrawal of the suturing needle. Hence, among the procedures which may benefit from the invention are subcuticular peritoneum, fascia closure, and skin closure.

While embodiments of the invention may include (or be used within) a powered or automated system, optionally making use of electromechanical power, hydraulic power, or the like (for example, with some embodiments being included within a robotic system), other embodiments may be configured for manual manipulation by one or more hands of a surgeon, often without having to resort to complex subsystems or external power.

Many embodiments of the devices described herein will be sterilizable so as to allow repeated use. Sterilization may be effected using autoclave techniques, chemical sterilization, irradiation, or the like, with most or all of the structures of the suturing device being formed of materials suitable for repeated sterilization (such as stainless steel, other metals and alloys, and the like). In general, the suturing device may comprise one or more plastics and/or metals common to surgical devices. Although specialized or proprietary suturing needles may be employed in some embodiments (for example, needles having flat gripping surfaces so as to maintain an alignment between the needle and an associated clamp), many embodiments of the suturing device will be suitable for use with standard off-the-shelf suture needles such as those packaged with any of a wide variety of permanent or resorbable suture materials in a hermetically sealed package. In fact, the invention may find some of its most immediate applications for facilitating surgical procedures performed manually in Third World countries, allowing physicians to treat a larger number of patients with greater ease than can be done using standard suturing techniques, but without the cost or complexity of recently-proposed automated suturing systems.

Referring now to FIG. 1A, an exemplary suturing device 101 is shown. Suturing device 101 comprises a clamp 3 for grasping a needle during a suturing procedure. Clamp 3 is actuated by handles 6 and 8. When device 101 is held in the hand of a surgeon, moving handles 6 and 8 together actuates clamp 3 to move jaws 25 toward each other so as to grasp a needle placed between opposing grasping surfaces of jaws 25. The jaws 25 typically include opposing needle grasping surfaces 53, which may be incorporated into the inside facing surfaces of the jaw or may be applied as an insert attached to the inside of each jaw. Clamp 3 further includes a needle contacting surface 50. In many embodiments, needle contacting surface 50 is defined by an offset that extends laterally outward from the jaw along an axis of the needle so as to contact the needle at a second location an axial distance from the point at which the needle is grasped between the jaws 25. By contacting the needle at a second location with needle contacting surface 50, clamp 3 provides resistance to twisting of the needle or pivotal movement of the needle about the needle grasping surface 53. Although needles come in various shapes and sizes, surgical needles are often formed with a curving shape between the proximal and distal ends. In many applications, the device 101 is used with a curved needle, the needle having a radius of curvature along its longitudinal axis, the axis defining a plane of curvature of the needle. For curved needles, a flat offset portion 60 may also provide resistance to rotation of the needle along its axis so as to maintain an alignment or orientation of a the plane of curvature of the needle relative to the device 101.

In this embodiment, clamp 3 comprises a pair of jaws 25 and a needle contacting surface 50 formed in one jaw 25, the needle contacting surface 50 defined by an offset in the jaw and extending laterally outward on one side of clamp 3. In alternate embodiments, the needle contacting surface may extend outward from both sides of clamp 3, or each jaw may define a needle contacting surface. In a preferred embodiment, each of jaws 25 comprises an offset portion defining needle contacting surface 50 such that the needle contacting surface 50 extends laterally outward from both sides of clamp 3. In many embodiments, the needle contacting surface 50 is designed so that a plane of the needle contacting surface 50 is transverse, preferably substantially perpendicular, to a plane of the clamping surfaces of jaws 25 so that the pivotal and rotational movement of the needle is effectively constrained. In an exemplary embodiment, the offset portion is substantially flat so that a needle received by clamp 3 will contact the flat needle contacting surface 50 extending laterally from both sides of clamp 3, so as to ensure proper positioning and alignment of the needle with clamp 3. Although in a preferred embodiment, the needle contacting surface 50 is defined by an offset portion of a jaw, it is appreciated that the needle contacting surface may comprise a member or structure separate from the jaw so long as the surface extends laterally outward from clamp 3 to constrain pivotal or rotational movement of a needle grasped within the clamp 3.

Figure 1B:
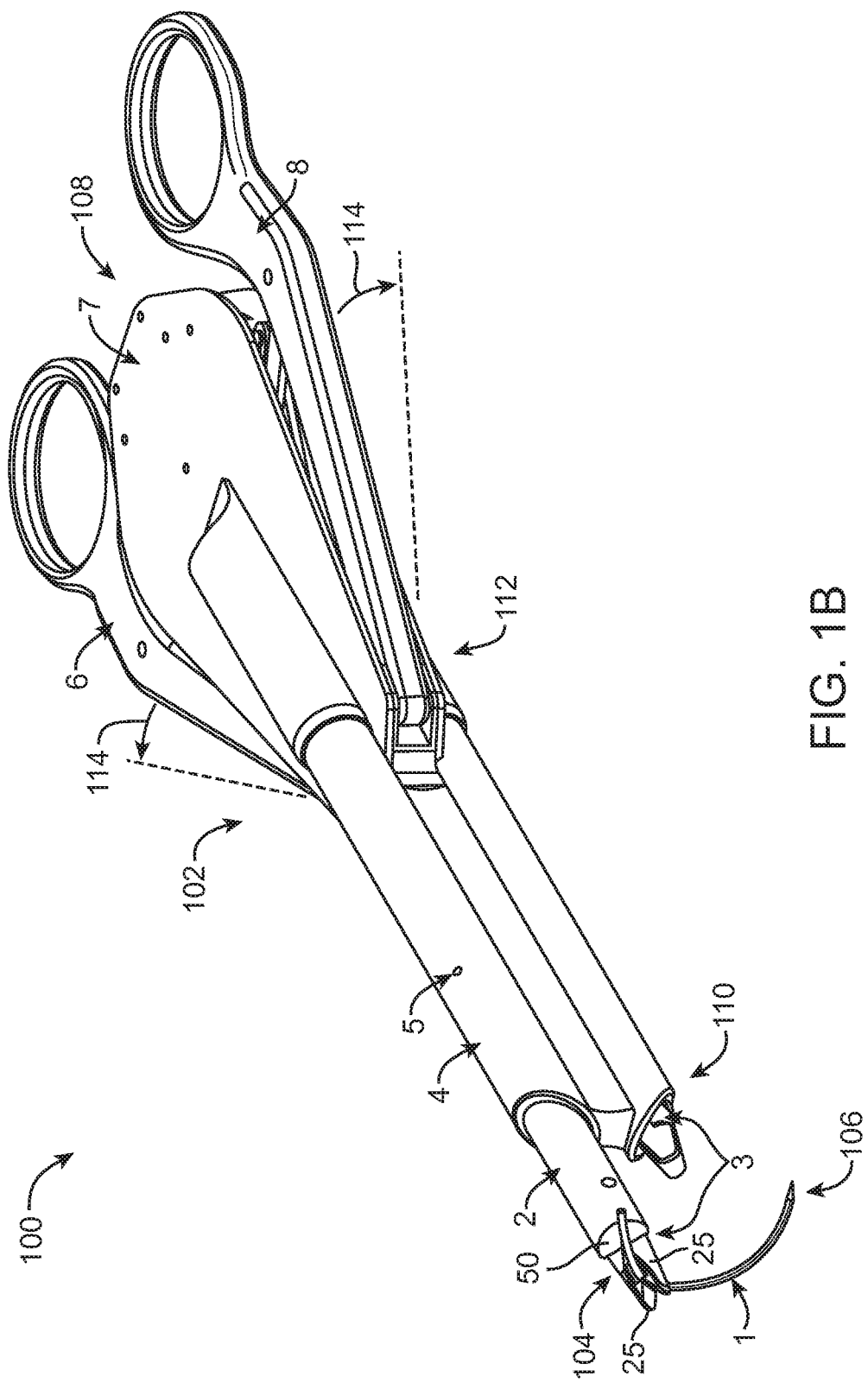
FIG. 1B is a perspective view of an exemplary suturing device having alternating clamps, each clamp having offset portions defining the needle contacting surface, in accordance with many embodiments.

Referring now to FIG. 1B, an exemplary suturing system 100 generally includes a suturing device 102 and a needle 1. Needle 1 generally has a proximal end 104 and a distal end 106, with at least the distal end being sharpened to facilitate insertion of the needle distally into and through tissues. Curved surgical needles, such as needle 1, are often packaged with a suture extending from proximal end 104, with the needle sometimes being referred to as an acus. Suturing device 102 typically has a body 112 having a proximal end 108 and a distal end 110. A pair of clamps 3 are disposed near the distal end 110, while first and second handles 6, 8 are disposed near proximal end 108. Each of clamps 3 includes a pair of jaws 25 and a needle contacting surface 50, such as those described above in device 101. Body 112 may include a proximal housing 7 and a distal extension 4. The distal extension having a pair of channels, with each channel reciprocatably receiving a shaft 2 supporting an associated clamp 3.

In this embodiment, clamps 3 are mirror-symmetric, although they may alternatively have differing shapes. Clamps 3 are generally offset so as to grip axially offset portions of needle 1B, with one of the clamps gripping a more proximal portion of the needle and the other clamp gripping a more distal portion of the needle. When handles 6, 8 are in a close-handed configuration as illustrated in FIG. 1, only one of clamps 3 will typically grip needle 1, the other clamp being retracted proximally away from the needle. Handles 6, 8 have openings for receiving fingers of the surgeon's hand, and the surgeon will typically actuate the handles by opening them from the closed-handed configuration shown to an open-handed configuration 114. Starting with handles 6, 8 in the closed (as shown in FIG. 1), when the handle is moved to open-handed configuration 114 and is then returned to the closed-handed configuration, the handle may be described as having completed an actuation cycle.

With each actuation cycle of handles 6, 8, the clamp 3 supporting needle 1 is alternated so that a needle initially supported by grasping the needle in first clamp along a proximal portion of the needle will, when handles 6, 8 are in open-handed configuration 114, instead be supported by the second clamp along a more distal portion of the needle. As handles 6, 8 move back to the closed-handed configuration to complete the cycle, the clamps again alternate, so that closing of the handle results in extension of the proximal clamp, gripping of needle 1 with that proximal clamp, release of the needle from the distal clamp, and retraction of the distal clamp. The position of needle 1 relative to body 112 may remain substantially fixed throughout the handle actuation cycle, although the shafts may move axially slightly as the needle goes from being held by one clamp, to both clamps, and then to the other clamp, with this movement of the needle being less than a length of the needle. When the needle is held by either clamp 3, the needle contacting surface 50 of the clamp contacts the needle to maintain the position and orientation of the needle 1 relative to the body of suturing device 102 during suturing. In this embodiment, each jaw of each clamp comprises an offset portion defining the needle contacting surface 50 (although each offset portion is not visible in FIG. 1B).

Figure 2:
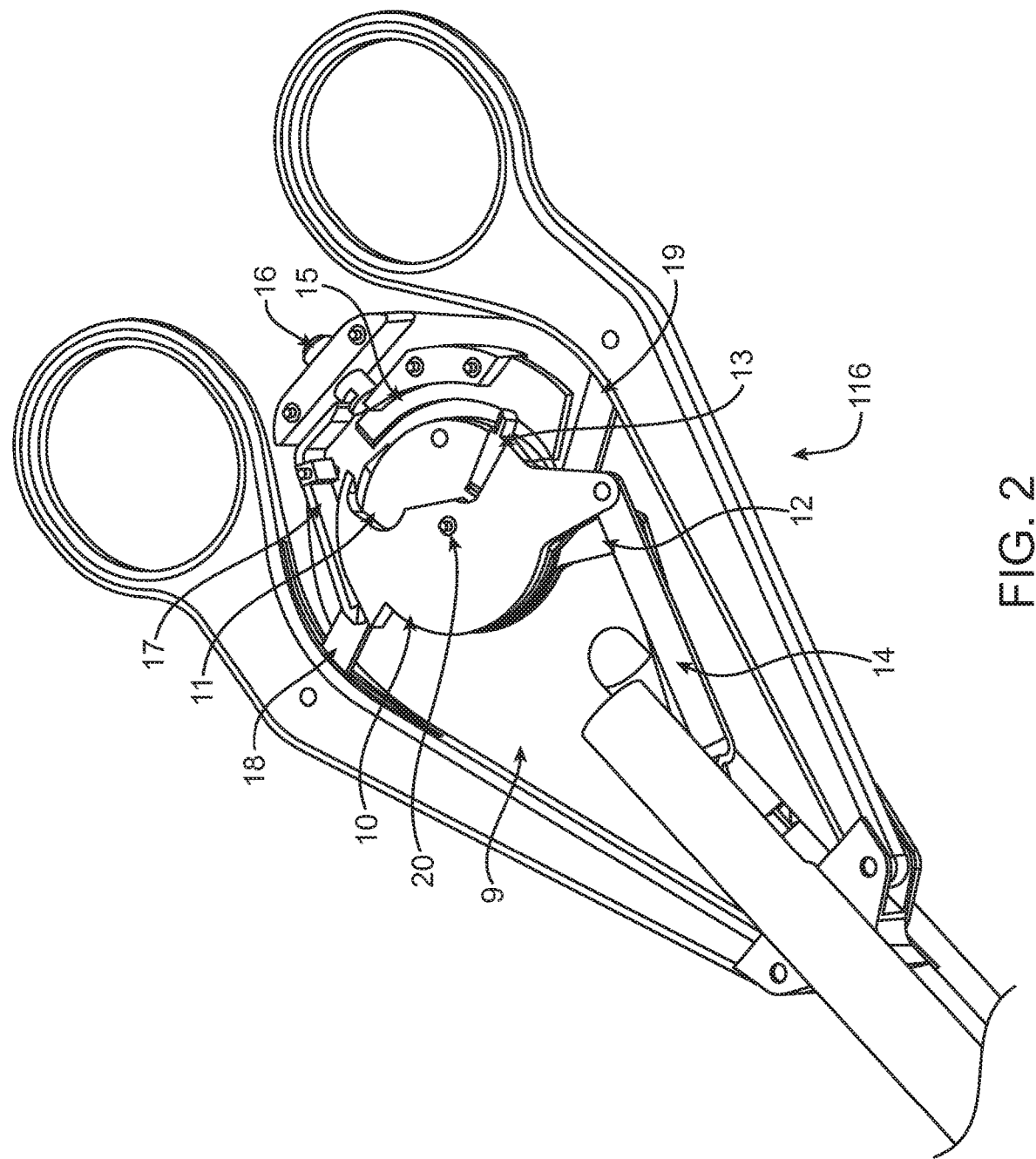
FIG. 2 is a perspective view of a proximal portion of the suturing device of FIG. 1B, with a cover removed from a proximal housing of the suturing device to show a portion of a linkage coupling a handle of the suturing device to the clamps of the suturing device.
Figure 3:
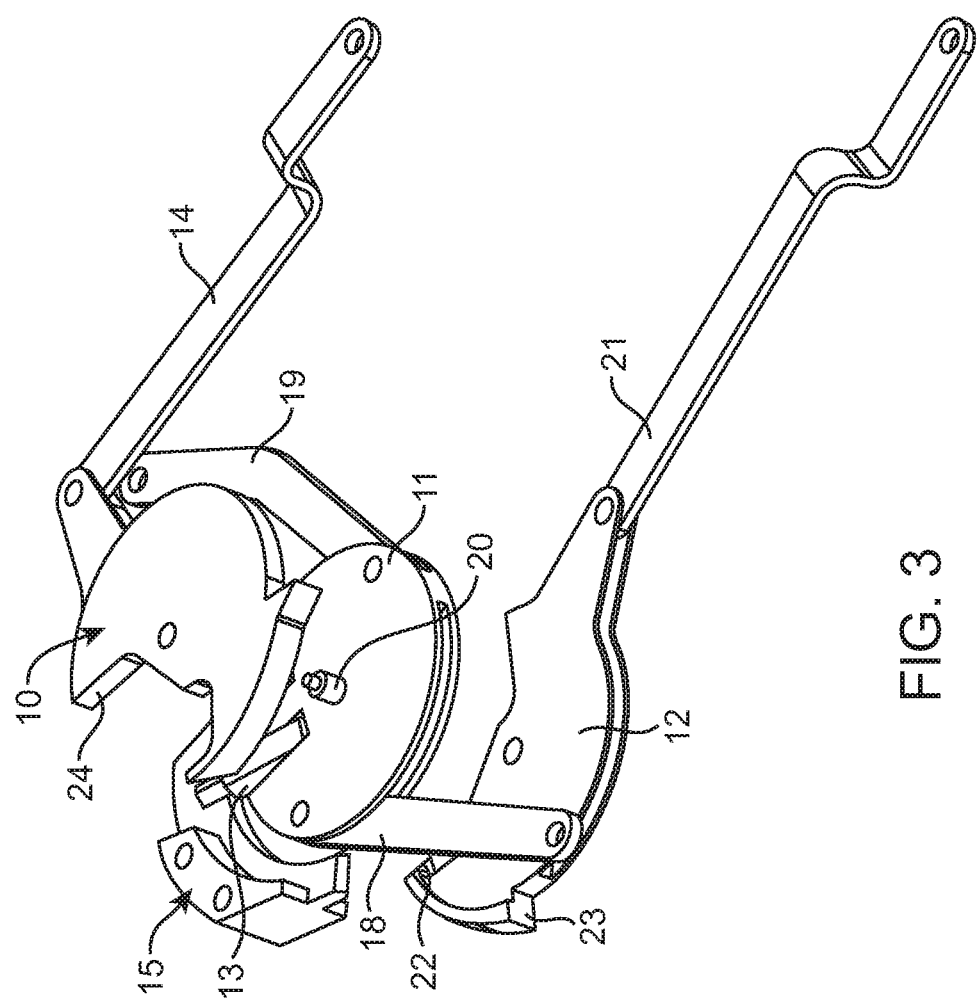
FIG. 3 is an exploded perspective view of components of the linkage shown in FIG. 2.
Figure 4:
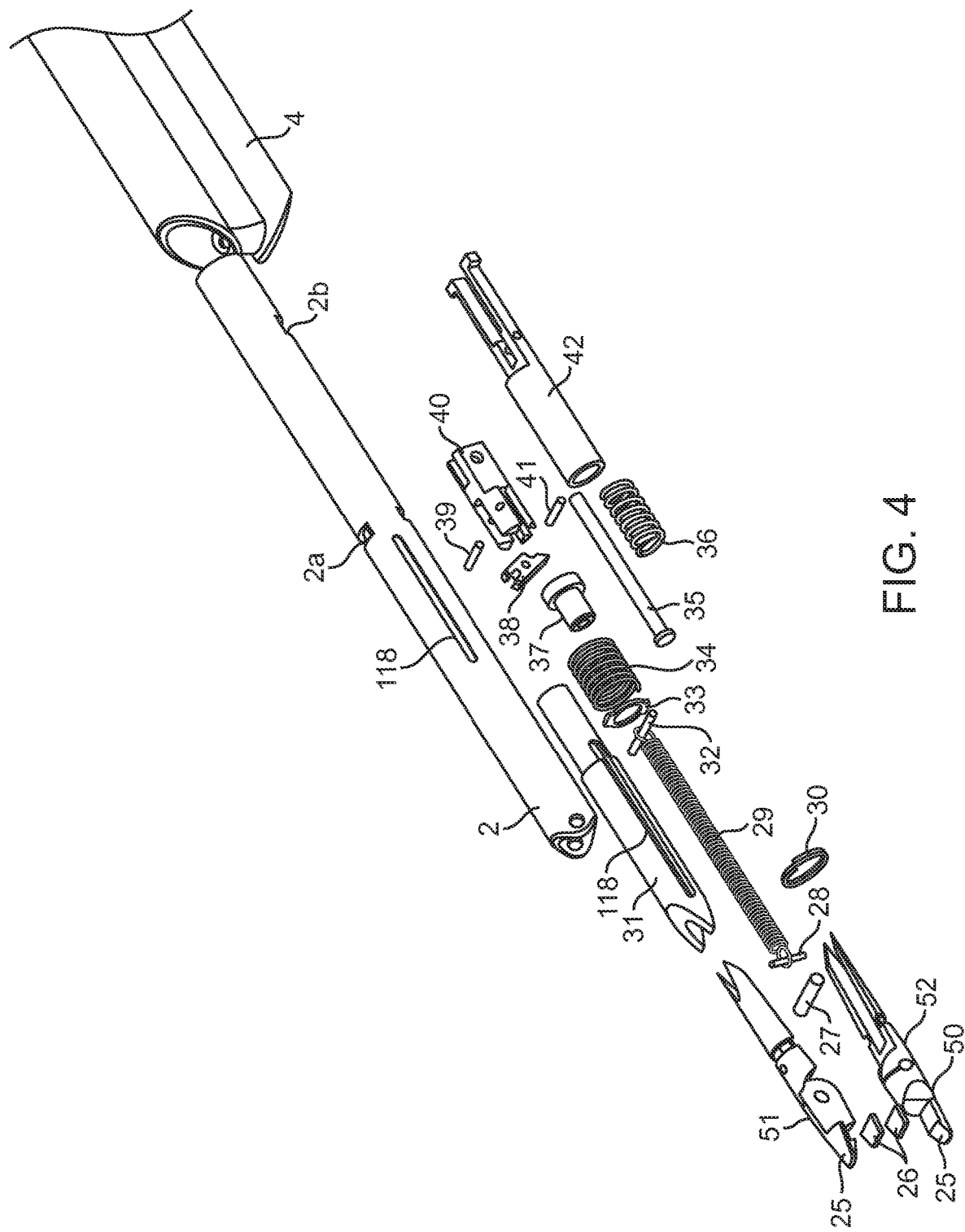
FIG. 4 is an exploded view of a distal portion of the suturing device of FIG. 1B, showing components of a clamp along with a reciprocatable shaft and elements of the linkage that effect movement of the reciprocatable shaft and actuation of the clamp.

Referring now to FIGS. 1B and 2, handles 6, 8 are pivotally attached to housing 7 of body 112. Housing 7 generally includes at least one lid 9 (the top lid shown removed in FIG. 2), with the proximal housing preferably including opposed first and second lids 9 on opposed major surfaces of the body. Lids 9 and the other structures of housing 7 generally enclose a drive linkage 116 coupling handles 6, 8 to clamps 3. In the embodiment of FIGS. 1-9, drive linkage 116 generally includes a drive wheel 11 and two driven wheels 10 and 12. The driven wheels 10 and 12 are mirror-symmetric and joined by tie rods 14 and 21 to clamps 3.

Referring now to FIGS. 1B-3, driven wheel 10 has a thrust surface 24, while driven wheel 12 has a stop surface 23 and an incline 22. The driving wheel is supported so as to rotate about an axle 20, the driving wheel also having a lug 13. The driving wheel 11 is coupled to handles 6, 8 by ties 18 and 19, so that actuation of the handles relative to the body 7 induces rotation of driving wheel 11 about the axle. The driven wheels 10, 12 rotate coaxially with driven wheel 11.

Lug 13 generally comprises an alternatable configuration driving element. Lug 13 either drivingly couples driving wheel 11 with driven wheel 10, or with driven wheel 12, depending on the configuration of lug 13 at the time. More specifically, when lug 13 is disposed above a guide 15 as shown in FIG. 2, the lug drivingly couples the driving wheel 11 with the upper driven wheel 10. When lug 13 is disposed below guide 15, the lug drivingly engages driven wheel 12, and is disengaged from driven wheel 10. A reset or release input button 16 interacts with guide 15 and a spring-loaded positioning arm 17 so as to allow both clamps 3 to release needle 1.

As can be understood with reference to FIGS. 1B-4, each clamp 3 is connected by an associated shaft 2 to the remaining components of drive linkage 116. Shafts 2 each include a lengthwise slot 118 (see FIG. 4), which allows the shaft to move within the channels of body extension 4. Guiding pins 32 ride in slots 118, and the guiding pins 32 are also fixed in extensions 4 within openings 5. Moving wedges 31 within shafts 2 also have lengthwise slots 118 for receiving guiding pins 32. The wedge surfaces of moving wedges 32 engage corresponding surfaces of working jaws 25, with the working jaws forming the open and closable structure of clamps 3. More specifically, distal movement of moving wedge 31 against a corresponding surface of working jaws 25 closes clamps 3, the working jaws being attached to a distal clevis of shaft 2 by axle 27. A spring ring 30 biases working jaws 25 to an open configuration, allowing them to move around and capture needle 1 before the working jaws are forced shut by the moving wedges.

Working jaws 25 may have a variety of surfaces for holding needle 1, the clamps preferably holding the needle so that movement of the needle relative to suturing device 100 is inhibited during stitching. The surfaces of working jaws 25 may be hardened by deposition of diamond or a diamond-like carbon, or inserts 53 of a material harder than that of working jaws 25 may be provided. Optionally, working jaws 25 may have hard-surfaced inserts comprising tungsten and/or cobalt, with the inserts optionally being fabricated using powder sintering or the like. A return spring 28 extends between pin 28 in working jaws 25 and the guiding pin 32, with the return spring partially fixed within a lumen of moving wedge 31. A spring 34 in the proximal portion of moving wedge 31 is held by a plug 37, with the distal end of spring 34 interacting with shaft 2 via thrust ring 33. Spring 34 can bring the moving wedge 31 into a position suitable for releasing the working jaws. A compensation spring 36 pressed against plug 37 writes on a rod 35 of a pusher 42 so as to maintain a desired axial force. Pusher 42 has an insert 40, which is connected with the pusher 42 by pin 39 and lug 38. The lug rotates about axle 41.

When handles 6 and 8 are moved apart to an open-handed configuration 114, a retracted clamp 3 and its associated shaft 2 moves from within a channel of body extension 4. While retracted, the moving wedge 31 is biased by spring 34 away from working jaws 25, so that spring ring 30 is free to open the clamp to allow it to extend around needle 1. Extension of compensating spring 34 may be at its greatest point while the associated clamp 3 is retracted, and insert 40 extends from pusher 42 with lug 38 in the insert. As handles 6 and 8 are brought together, driving wheel 11 is turned by connector ties 18, 19. Lug 38 interacts with thrust surface 24 of driven wheel 10 and moves the driven wheel 10 in rotation. The motion of driven wheel 10 is transferred by tie rod 14 so as to move insert 40 axially along body extension 4. The insert, in turn, moves the pusher 42 along body extension 4, the relative position of the insert 40 and pusher 42 being maintained by an inner surface of shaft 2 interacting with plug 30 so as to inhibit rotation of the plug about axle 41. Pusher 42 presses spring 34 and compensation spring 32, and via plug 37 and thrust ring 33, moves shaft 2. The movement of shaft 2 overcomes spring 29 and extends the shaft from the channel of body extension 4.

During distal movement of pusher 42, spring 34 and compensating spring 36 are sufficiently stiff so as to inhibit elongation, as their spring coefficients are significantly higher than that of return spring 29. However, engagement between an end of slot 118 in shaft 2 and guiding pin 32 eventually inhibits further distal movement of the shaft. Once shaft 2 has stopped its distal movement (due to engagement of lengthwise slot 118 with guiding pin 32), spring 34 begins to contract, its rigidity being lower than that of compensating spring 26. As a result, moving wedge 31 begins to extend distally relative to working jaws 25, the corresponding surfaces of the wedge and working jaws sliding against each other so as to move the proximal ends of the working jaws apart and bringing the distal needle gripping inserts 26 of working jaws 25 together so as to grasp needle 1. As spring 34 contracts, contraction of compensation spring 36 also begins and the insert 40 moves. When lug 38 extends into and/or engages window 2a of shaft 2, pusher 42 engages a surface of body extension 4 or proximal housing 7, and axial movement of the pusher stops. Insert 40 continues moving, so that lug 38 rotates around axle 41. The lug interacts with an edge of shaft 2 and, overcoming compensation spring 36, starts to draw shaft 2 and its contents into body extension 4.

The clamping force on needle 1 by clamps 3 may be determined by the spring characteristics of compensating spring 36 so as to remain within a desired range. Advantageously, the clamping force imposed by suturing device 100 on needle 1 may correspond to forces applied by standard needle holders. Thrust surface 23 of driven wheel 12 approaches a tooth of spring-loaded fixing arm 17, and overcoming the spring, the thrust surface passes under the tooth, releasing the tooth so that the tooth and thrust surface are positioned for neutral engagement. After the thrust surface 23 of the driven wheel 12 passes beyond the tooth of spring loaded fixing arm 17, engagement of the thrust surface and tooth inhibit the return of the driving linkage 116 to its prior configuration, thereby inhibiting the release of needle 1 from the closed working jaws 25 so that the needle is not dropped.

As handles 6, 8 continue to move toward the open-handed configuration of the handle actuation cycle, movement of driven wheel 12 is inhibited by spring-loaded fixing arm 17. Driving wheel 11 nonetheless turns, and is reset. More specifically, incline 22 of driven wheel 12 moves lug 13 from a configuration above guide 15 to a configuration in which the lug is disposed under the guide. Hence, when handles 6, 8 continue to move, here towards a closed-handed configuration, the lug 13 will interact with thrust surface 24 of the driven wheel 10. The description above regarding driven wheel 12 is thus repeated but with driven wheel 10 instead. When moving under the spring-loaded fixing arm 17, the thrust surface 23 of driven wheel 12 lifts the spring-loaded fixing arm 17 and releases driven wheel 10.

By action of spring 34, moving wedge 31 is retracted proximally from between the proximal ends of working jaws 25, so that the proximal ends of the working jaws are brought together by spring-loaded ring 30. Distal ends of working jaws 25 thereby move apart and the needle is released. Each repeated opening and closing actuating cycle of handles 6, 8 alternates the needle between being held by one, and then the other of clamps 3, and often back to the first clamp. In other embodiments, each handle actuation cycle effects transfer of the needle from one clamp to the other, with the needle returning to be held solely by the first clamp only with a second handle actuation cycle. Regardless, during each cycle each retracted clamp is preferably extended around an associated portion of needle 1 and is closed before the previously extended clamp opens, so that the needle is held continuously by at least one of clamps 3 throughout the handle actuation cycle.

If it is desired to release needle 1 from suturing device 112 at any time during, before, or after a handle actuation cycle, release can be effected by pressing on release input button 16. Pressing on button 16 causes spring-loaded fixing arm 17 to lift away from driven wheels 10 and 12, thereby resetting the clamps in their proximal opened configuration.

Figure 5:
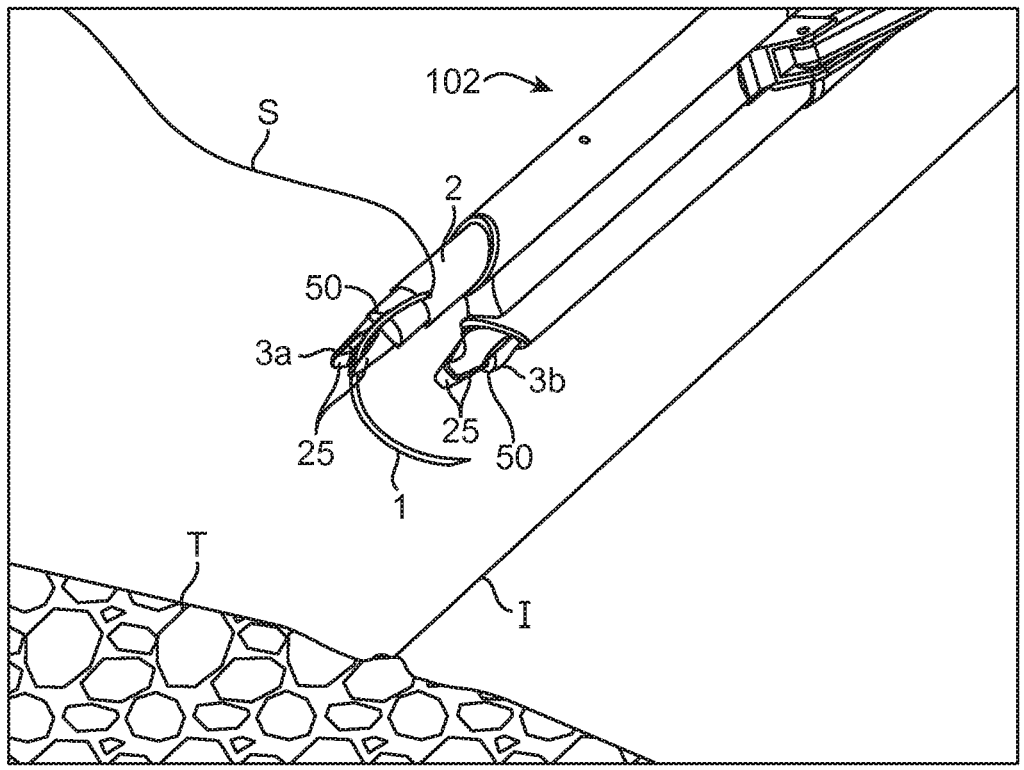
FIGS. 5-9 are perspective views showing use of an exemplary suturing device for suturing tissues, in accordance with many embodiments.

Referring now to FIGS. 5-9, the use of suturing device 102 for suturing an incision 1 in tissue T can be understood. Initially, handles 6, 8 (see FIG. 1) are in a closed-handed configuration and the handles are grasped by a hand of a surgeon. Needle 1 is supported by a first clamp 3a, with the first clamp grasping a proximal portion of the needle at a first location adjacent a suture S. The second clamp 3b is retracted proximally away from needle 1, so that a distal portion of the needle is free and exposed, as illustrated in FIG. 5.

When the proximal portion of the needle is placed within clamp 3a between jaws 25, the needle contacts the offset portions 50 of each jaw 25, the offset portions defining the needle contacting surfaces 50, which extend laterally outward from either side of clamp 3a. The needle contacting surface 50 of the offset portions verifies the proper positioning and/or orientation of the needle relative the device 102. In the embodiment shown in FIG. 5, the needle contacts the offset portions 50 such that the plane of curvature of the needle 1 is substantially perpendicular to the grasping surface of the jaws 25, as well as perpendicular to a longitudinal axis of shaft 2. By contacting the needle with surface 50 of the clamp, a physician may verify proper positioning and alignment of the needle 1 for a given device before suturing. It is appreciated that the needle contacting surface 50 could be configured to position that needle relative to the body of suturing device 102 in various positions or alignments as desired for a given procedure or anatomy.

Figure 6:
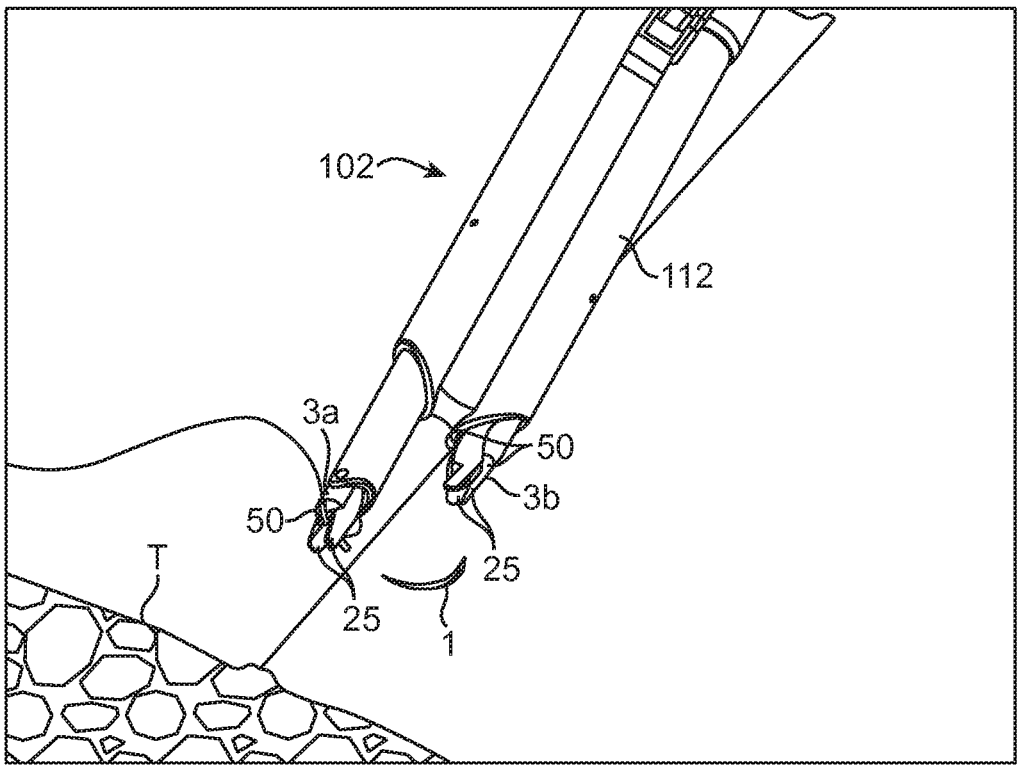

As can be understood with reference to FIG. 6, the surgeon manually moves suturing device 102 by manipulating handles 6, 8 so as to insert a distal portion of suturing needle 1 through tissue T. Advantageously, the offset portions 50 of each jaw 25 of clamp 3a inhibit movement of needle 1 relative to the body of device 102 while the needle is pushed through the tissue. This allows the surgeon to precisely control movement of the needle 1 as it is inserted through the tissue, in a manner analogous to manual manipulation of the needle using a standard needle grasper or forceps. As the needle 1 is pushed through the tissue T it may encounter various resistive forces exerted by the tissue. Additionally, as the needle 1 penetrates the tissue T, movement of the body of the device 102 by the physician may cause reaction forces between the tissue T and the needle 1. These forces may apply a torque in either direction, which absent the offset portions 50, might cause the needle to pivot or rotate relative to the jaws or cause rotation of the needle 1 about its axis. By contacting the needle 1 at a second location on the needle 1 an axial distance away from the first location, the clamp 3a is able to apply a countering torque to resist the torque and twisting forces applied by the tissue. Generally, the further outward the offset portions 50 extend (along an axial direction of the needle), the more torque the clamp 3a is able to withstand. In many embodiments, the needle contacting surface of the offset portions 50 extend laterally outward from the edge of the jaw by at least $\frac{1}{8}^{th}$ the width of the grasping surface of the jaw as measured along an axis of the needle grasped within the jaw. Preferably, the offset portions 50 extend an axial distance of at least half the width of the grasping surface of the jaw, and even more preferably between half and twice the width.

Figure 7:
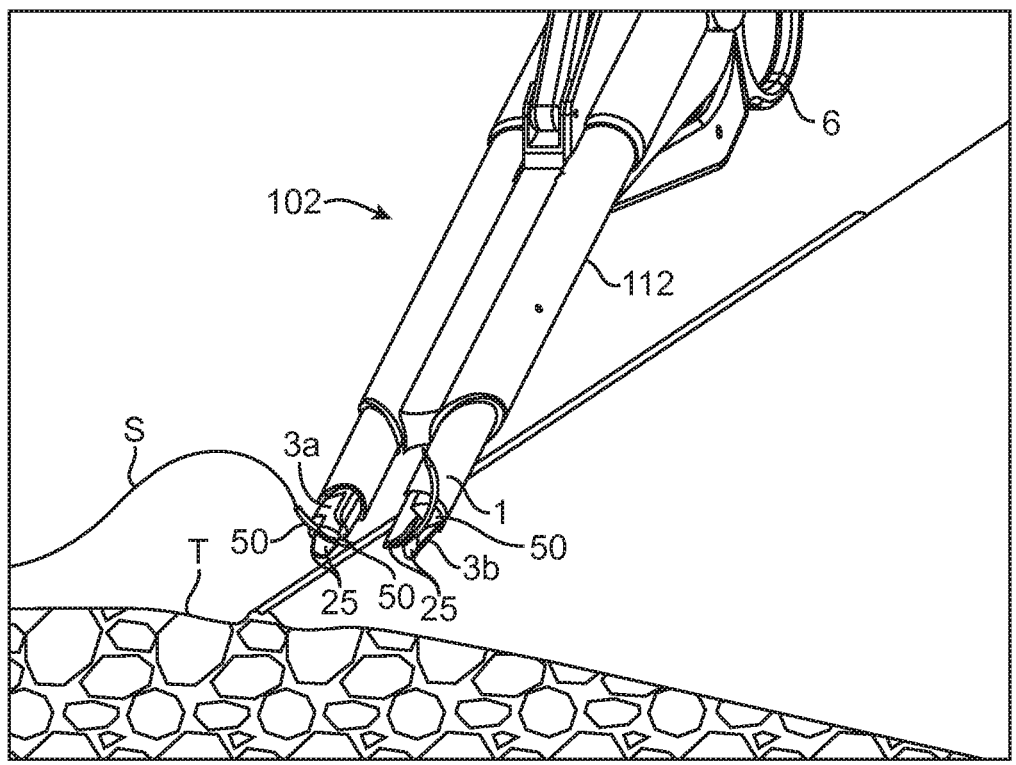

As can be understood with reference to FIGS. 6 and 7, once the distal portion of needle 1 extends sufficiently through the tissue T, handles 6, 8 can be cycled through at least a portion of their actuation cycle. Through the linkage 116, second clamp 3b is extended distally from body 112 of suturing device 102, grasping the distal portion of needle 1 between jaws 25 of clamp 3b, while offset portions 50 of clamp 3b contact the needle to verify the position of the needle grasped in clamp 3b and to maintain the position and orientation of the needle 1. The first clamp 3a then releases needle 1 and is withdrawn proximally from around the needle, as illustrated in FIG. 8.

Figure 8:
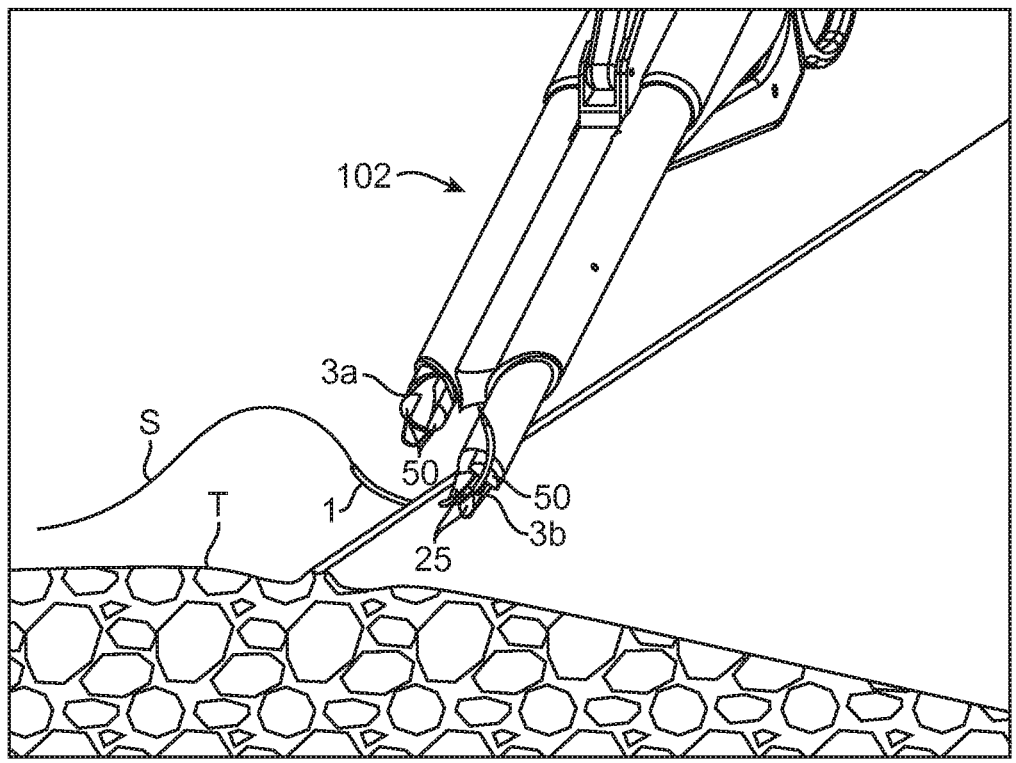
Figure 9:
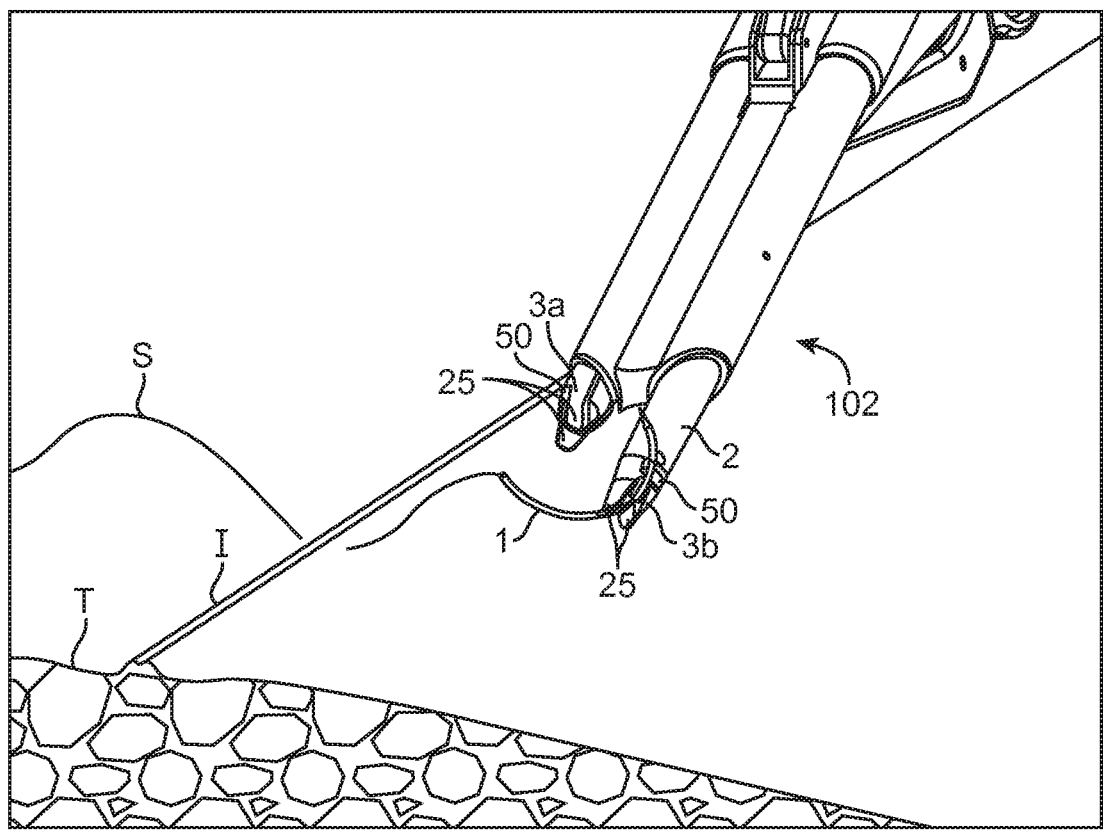

As can be understood with reference to FIGS. 8 and 9, once needle 1 is held by second clamp 3b, the surgeon can again manipulate the needle by moving handles 6, 8. In some embodiments, the surgeon can grasp the handles in an open-handed configuration while pulling the needle free from the tissue, while in other embodiments the needle will be pulled after the handle has returned to the closed-handed configuration. Regardless, the surgeon uses the handles, body, and clamp 3b to pull the proximal portion of needle 1 through tissue T, thereby leaving suture S inserted across incision 1. As the proximal portion of the needle 1 is withdrawn from the tissue T, the needle 1 again encounters various forces and torques applied in part by the tissue T and the suture being pulled through the tissue. The offset portions 50 of clamp 3b inhibit movement of the needle 1 relative to the body of the device 102 by countering the torques and forces the needle 1 encounters as it is drawn through the tissue T, as described with reference to clamp 3a above.

Prior to initiating a second stitch, the surgeon will often pull the needle away from the incision 1 of the tissue T to pull the suture taught. In pulling the suture taught, the suture will exert significant force on the needle to which it is attached. The offset portions 50 (or other such needle contacting surface) counter this force and torque on the needle, as described above with reference to clamps 3a and 3b above, so as to maintain the position and orientation of the needle 1. The surgeon will then typically alternate clamps to support the proximal portion of the needle 1 with clamp 3a before starting the next stitch.

To alternate clamps, the surgeon can cycle handles 6, 8 by closing the handles with his/her hand, or by opening and closing the handles through a full actuation cycle. This results in grasping of needle 1 by first clamp 3a and release of the needle by second clamp 3b, exposing the distal portion of the needle and displacing the second clamp from the needle so that the needle is ready to again insert through tissue T, as can be understood with reference to FIG. 5. The process can then be repeated without ever having to completely release needle 1, and by simple actuation of handles 6, 8 after insertion of the distal portion of the needle through the tissue and again after pulling the needle through the tissue T. The process is repeated to form as many stitches as is desired. Analogous insertion of the distal portion of the needle through loops of suture, actuation of the handle, and pulling the needle free can be used to quickly and easily form knots. By maintaining proper alignment of the needle 1 by inhibiting movement of the needle, including pivoting of the needle about the jaws 25 or rotation of the needle about its axis, the device 102 facilitates suturing with the device while increasing ease of use and accuracy of suturing.

As can be understood from the illustrations in FIGS. 5-9, and as may be indicated by the detailed description above of the articulation of the drive linkage, shafts 2 extending distally from body 112 to clamps 3a, 3b may move slightly during the handle actuation cycle, for example, with the shaft supporting the clamp initially holding needle 1 retracting slightly into body 112 as the other shaft extends. Nonetheless, each clamp holds the needle at a fixed location with opposing grasping surfaces of the jaws and with the needle contacting surface 50 of the clamp while the surgeon holds the handles 6, 8 in the closed configuration and inserts or withdraws the needle into or from the tissue.

In accordance with many embodiments, the device 102 may utilize a wide variety of alternative linkage mechanisms, clamp structures, housing, handles, and the like for actuating the clamps and/or alternating grasping the needle between clamps. For example, alternate mechanisms and clamping structures, including quick disconnect interfaces, removable cartridges, and latches for removably supporting a plurality of clamps in a single clamp unit, can be seen in more detail in U.S. Pat. No. 7,588,583 issued on Sep. 15, 2009; U.S. patent application Ser. No. 11/532,032 filed Sep. 14, 2006; U.S. patent application Ser. No. 12/535,499 filed Aug. 4, 2009; U.S. patent application Ser. No. 12/049,552 filed on Mar. 17, 2008; U.S. patent application Ser. No. 12/049,545 filed on Mar. 17, 2008; U.S. patent application Ser. No. 12/687,349 filed on Jan. 14, 2010; and U.S. Patent Application 61/358,764 filed on Jun. 25, 2010, the full disclosures of which are incorporated herein by reference in their entirety. One of skill in the art would appreciate that the present invention may be incorporated into any of the alternative needle grasping tools disclosed herein, or in various other needle grasping tools.

Figure 10:
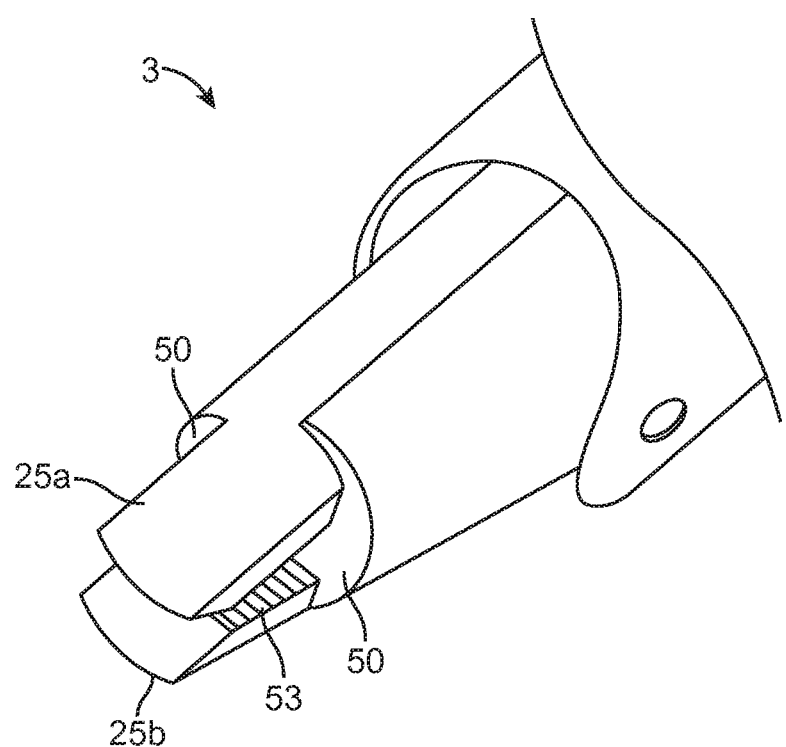
FIG. 10 is a perspective view of an exemplary clamp in an alternative suturing device having first and second alternatable clamps, each jaw of the clamp having an offset portion defining the needle contacting surface.

FIG. 10 illustrates an exemplary embodiment of a clamp 3 of suturing device 102. The clamp comprises jaws 25a and

25b, each jaw having a flat offset portion defining a needle contacting surface 50. Preferably, the offset portion 50 extends laterally outward from clamp 3 such that the surface is perpendicular to a grasping plane extending along grasping surface 53 of the jaws. Although the flat offset portion 50 shown is semi-circular, it is appreciated that the needle contacting surface 50 may be any shape so long as a needle grasped between jaws 25a and 25b at a first location contacts the surface at a second location an axial distance away from the first location.

Figure 11A:
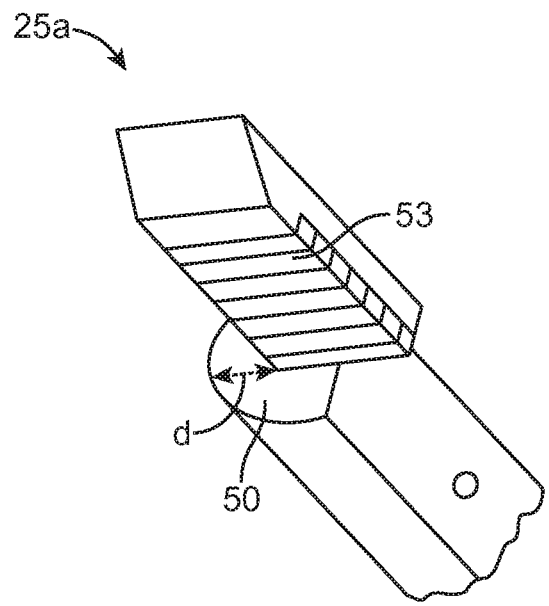
FIGS. 11A-11B show the first and second jaws of the exemplary clamp of FIG. 10.

FIG. 11A illustrates jaw 25a of clamp 3 in FIG. 10. The proximal portion of jaw 25a may be attached to the actuation mechanism, such as with a shaft, so that actuation of the mechanism moves jaws 25a and 25b toward each other so as to grasp a needle therebetween. The offset portion defining the needle contacting surface 50 extends laterally outward a distance away from the grasping surface 53 of jaw 25a. The amount of torque and rotational force that the clamp 3 can withstand is determined partly on the distance, d, by which the needle contacting surface 50 extends from the jaw grasping surface 53. In many embodiment, d is at least $\frac{1}{8}^{th}$ the width of the jaw grasping surface, preferably at least half the width, and even more preferably between half and twice the width of the jaw grasping surface.

Figure 11B:
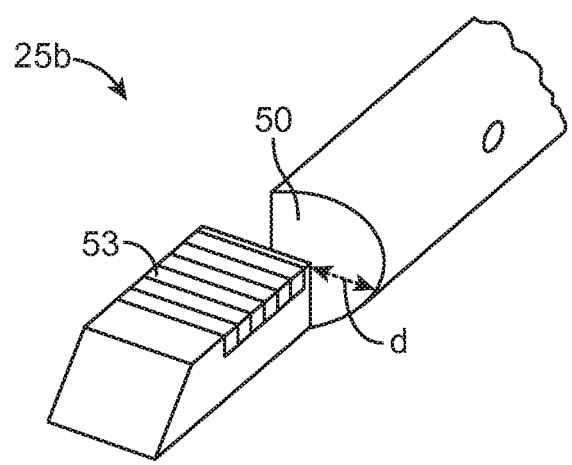

FIG. 11B illustrates jaw 25b of clamp 3 in FIG. 10. Similar to jaw 25a, the proximal portion of jaw 25b includes a shaft by which an actuation mechanism of device 102 can move jaws 25a and 25b toward each other so as to grasp a needle therebetween. The offset portion defining the needle contacting surface 50 extends laterally outward a distance, d, away from the grasping surface 53 of jaw 25b. In many embodiments, jaw grasping surface 53 includes a textured surface for grasping the needle more effectively. The textured surface may include grooves, marking, scorings or indentations that engage a needle grasped between the jaws. In some embodiments, the jaw grasping surface may comprise a separate insert attached to the inside of each opposing jaw. In an exemplary embodiment, the dimensions of jaw 25a and 25b are similar or mirror-symmetric such that each jaw corresponds with the opposing jaw, although it is appreciated that the dimensions and overall geometry of opposing jaws may differ. For example, the needle contact surface 50 may comprise a separate member or structure, or a needle contacting surface 50 extending outward on either side of the jaws could be incorporated into one of a pair of jaws.

Figure 12A:
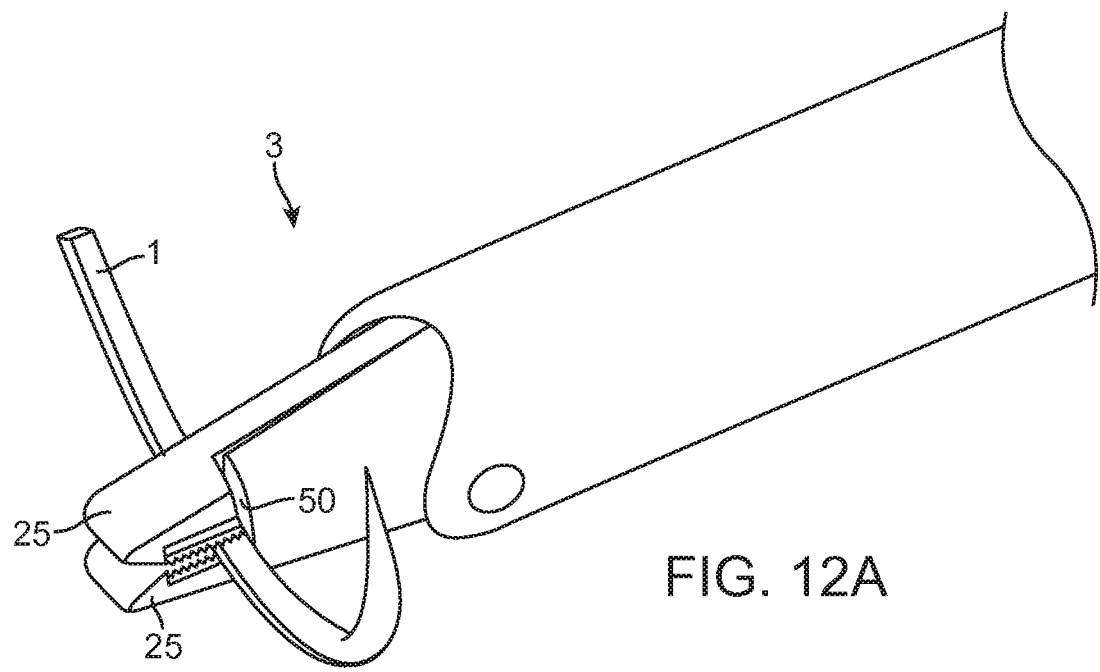
Figure 12B:
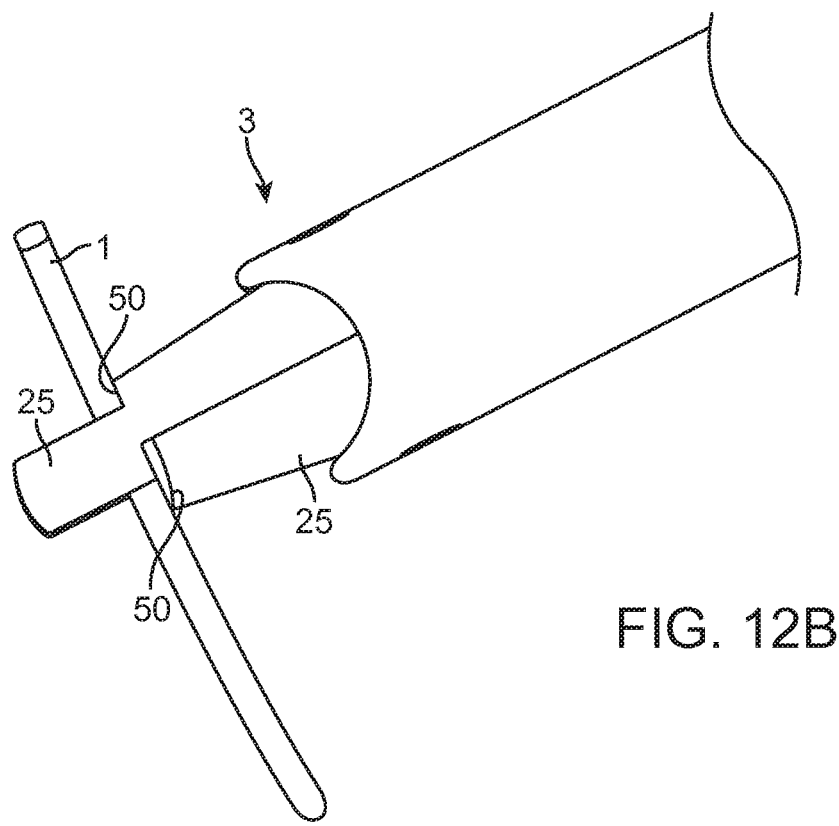

FIGS. 12A-12C illustrate the exemplary clamp 3 of FIG. 10 grasping a curved needle 1 between jaws 25. FIG. 12C shows a detail of clamp 3 grasping needle 1 showing the contact point of needle 1 along the needle contacting surface 50 defined by the offset portion extending laterally outward from the clamp along the axis of the needle.

Figure 13:
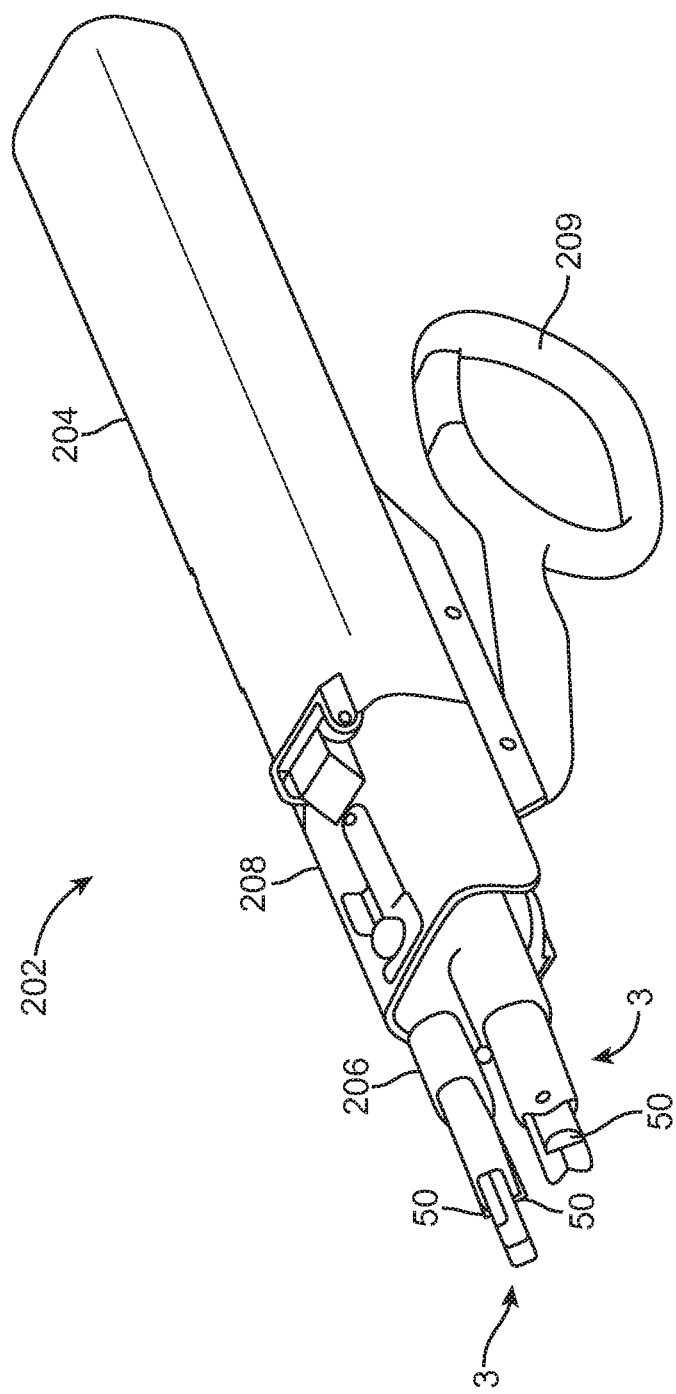
FIG. 13 is a perspective view of an alternative embodiment.

Referring now to FIG. 13, an alternative suturing device 202 may include many functional components which are similar to those described above, but can generally be separated into a reusable drive unit 204 and a disposable clamp unit 206. A releasable coupler 208 releasably couples clamp unit 206 to the drive unit 204. The exemplary coupler includes an interface that provides rigid coupling between extensions 210 of the clamp unit 206 and proximal housing 212 of drive unit 204, and also provides moving engagement surfaces between the shafts of the clamp unit and axially moving elements of the drive linkage. While the exemplary releasable coupler 208 includes axial positioning surfaces (in the form of a pin of drive unit 204 and corresponding aperture of clamp unit 206) and a releasable latch to avoid inadvertent decoupling, a wide variety of alternative releasable couplers might also be employed. The exemplary clamp unit includes two clamps 3, each clamp having a needle contacting surface 50 extending laterally from the clamp in an axial direction from each side of the clamp. In some embodiments, each clamp may be individually attached to a drive unit 204. Regardless, allowing the clamps to be detached from the drive unit can avoid any need for making the clamps sterilizable, decreasing overall costs of the suturing system and helping to ensure that cross-contamination between patients is inhibited. A plurality of clamp units 206 will often be used with each drive unit 204, with each clamp being used for a single patient and then being disposed of. In this embodiment, device 202 comprises a handle 209 attached to an actuation mechanism for alternating between grasping a needle with the first and second clamps 3. Preferably, the surgeon holds the drive unit 204 with one hand and uses a finger to cycle the actuation mechanism with handle 209. The device 202 may be used to drive the needle through the tissue, to pull the needle and suture through the tissue and to tighten the suture by moving the drive unit 204 while the needle is grasped in the first or second clamp 3.

Figure 14A:
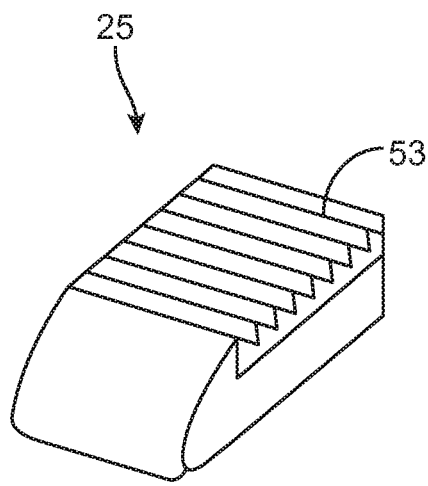
FIGS. 14A-14D are perspective and cross-sectional views of an exemplary clamping surface of a jaw of a clamp and a triangular needle grasped between the jaws of the clamp, in accordance with many embodiments.
Figure 14B:
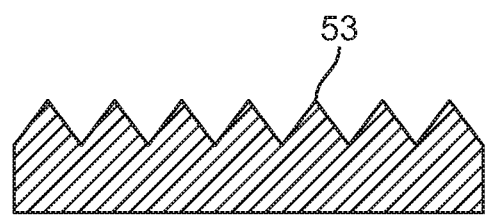
Figure 14C:
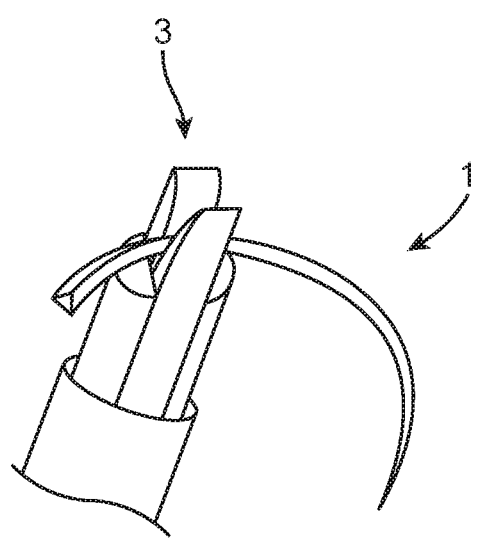
Figure 14D:
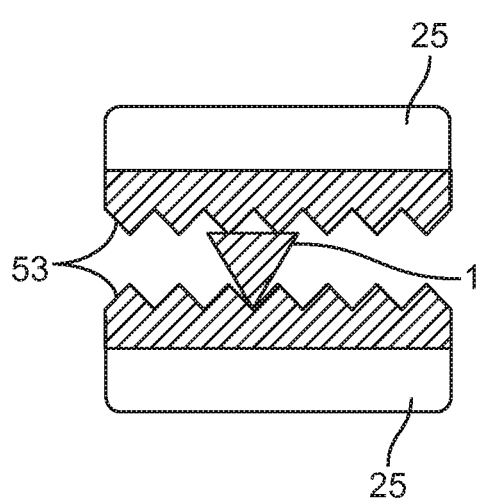
Figure 15A:
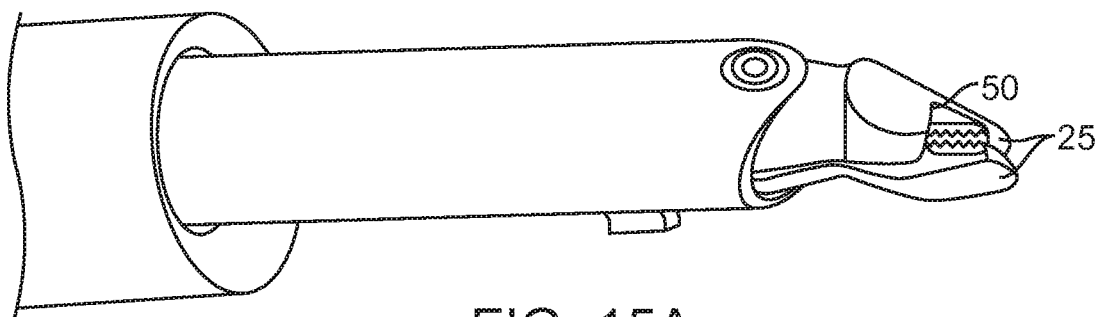
FIGS. 15A-15D are photographs of an alternative embodiment having curved jaws.
Figure 15B:
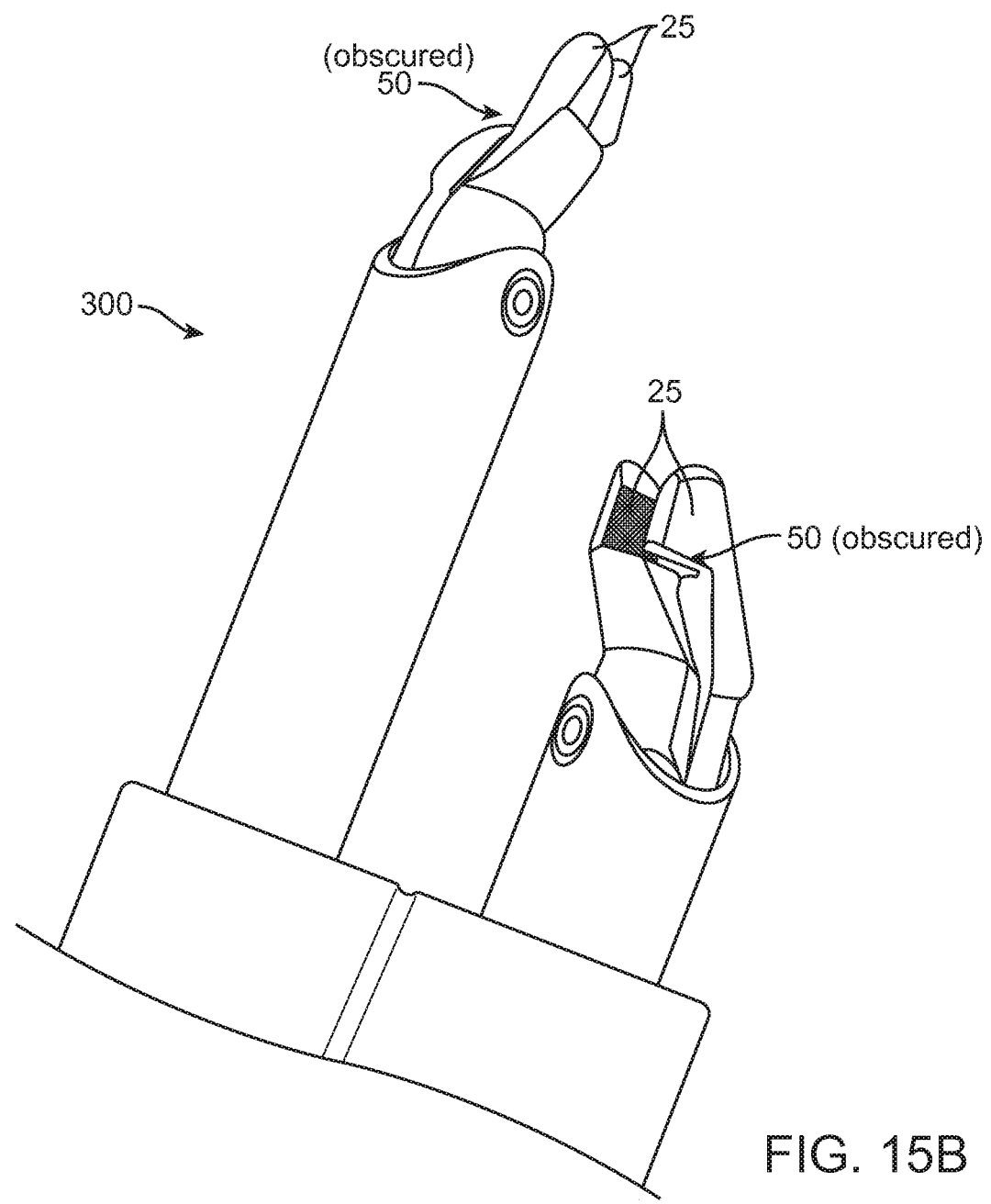
Figure 15C:
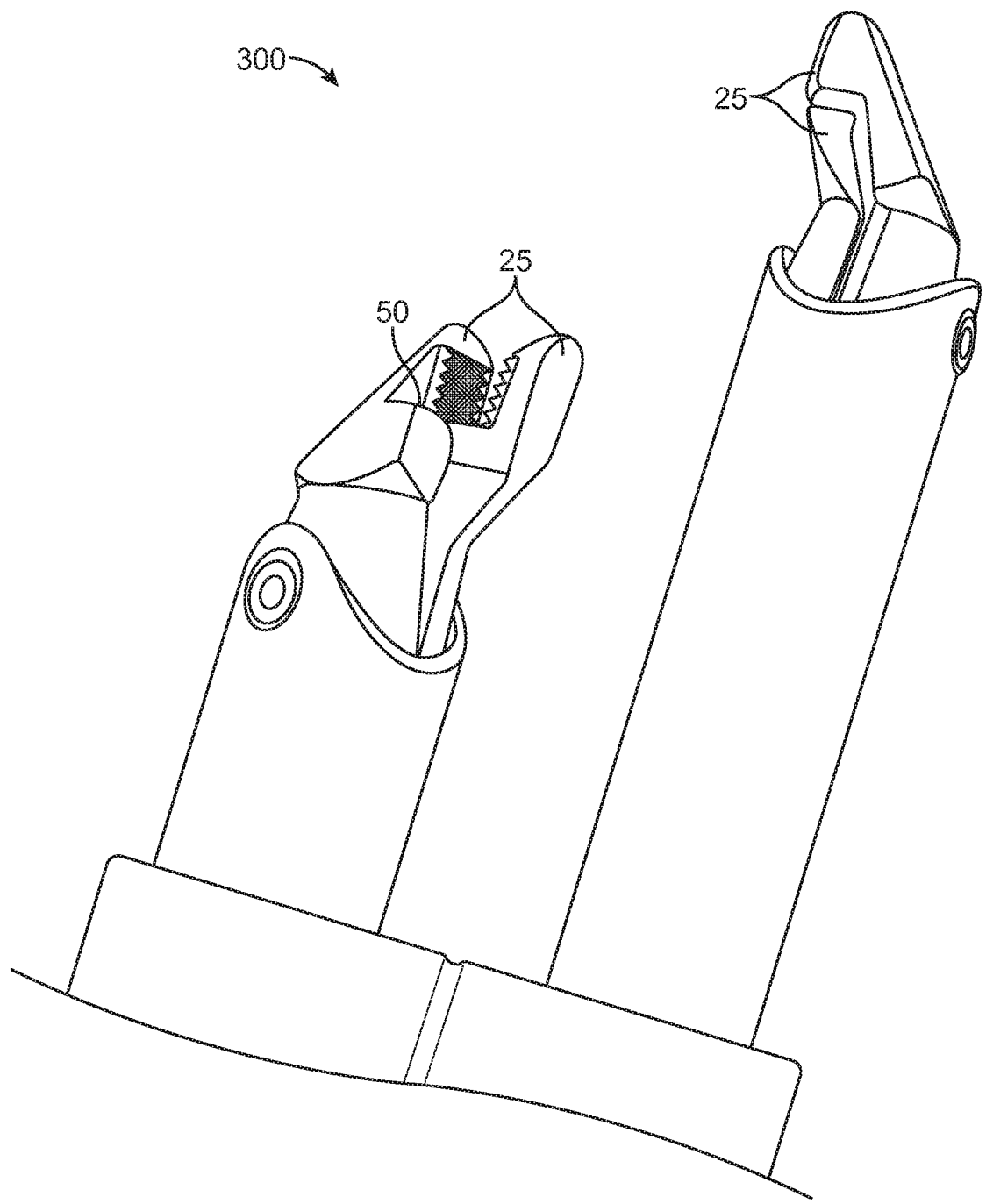
Figure 15D:
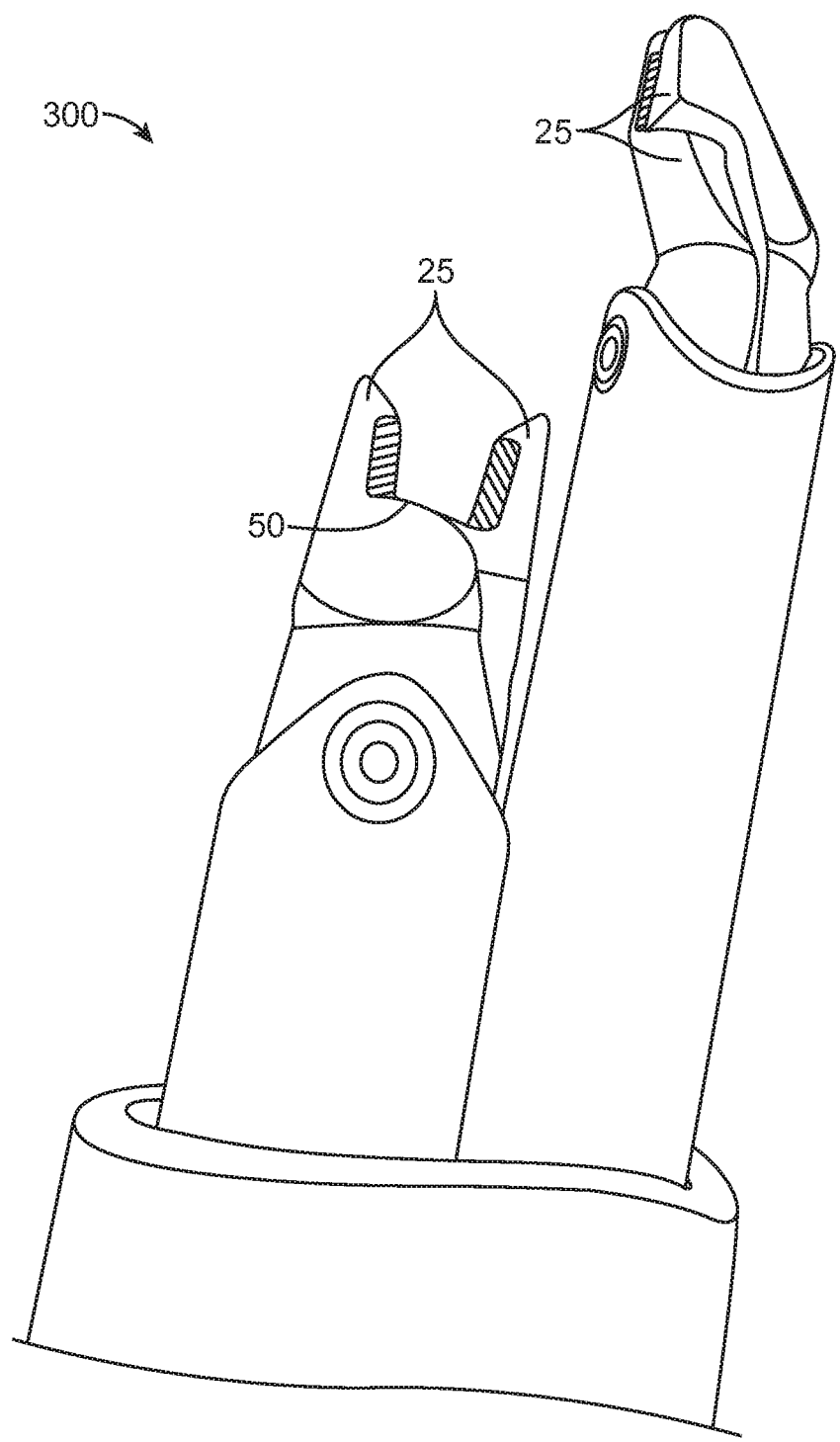

FIGS. 14A-D illustrate an exemplary embodiment of the jaw grasping surface 53 and its use. In one embodiment, the jaw grasping surface 53 comprises a series of ridges extending in the direction of a longitudinal axis of the needle 1 when grasped within the jaws 25. The jaw grasping surface 53 may be incorporated into the inside surface of the jaw 53, or may comprise a separate insert attached and optionally removable from the jaw 25. The ridges may be dimensioned so as to engage and receive a portion of the needle such that the ridges correspond to a geometry of the needle 1 used for a given application. For example, semi-circular ridges would correspond to a needle having a circular cross-section such that a circular needle grasped between two jaw grasping surface having semi-circular ridges would fittingly receive and grasp the needle. In a preferred embodiment, the jaw grasping surface 53 comprises triangular ridges, as shown in FIG. 14A and in the cross-section of FIG. 14B. A clamp having jaw grasping surfaces 53 with triangular ridges is particularly useful for grasping and engaging a needle having a triangular cross-section, as shown in FIG. 14C. FIG. 14D illustrates a cross-section of the clamp 3 of FIG. 14C grasping the needle 1 having a triangular cross-section. When grasped by clamp 3, an apex of the triangular cross-section of needle 1 is received by a triangular ridge of the grasping surface 53 thereby securing the needle between jaws 25. Jaw grasping surfaces 53 having triangular ridges are advantageous over the semi-circular grooves described above, since triangular ridges inhibit rotation of the needle along its axis when engaged with an apex of the triangular cross-section of the needle. It is appreciated that the above described jaw grasping surface having triangular ridges may be incorporated into any of the embodiments of the invention described herein, as well as in various other needle grasping devices.

Figure 16A:
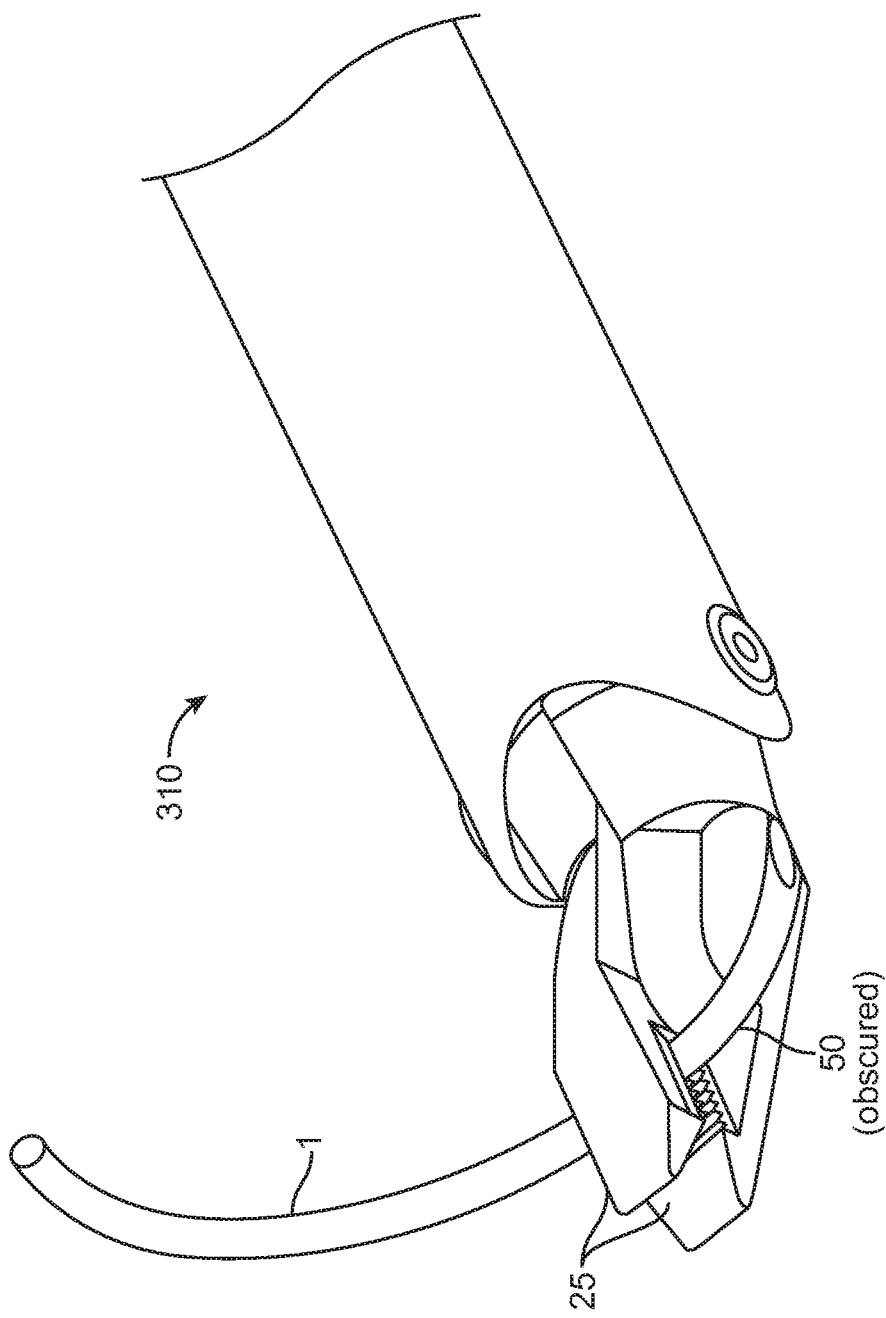
FIGS. 16A-16C illustrate detail views of an alternative embodiment having curved jaws.
Figure 16B:
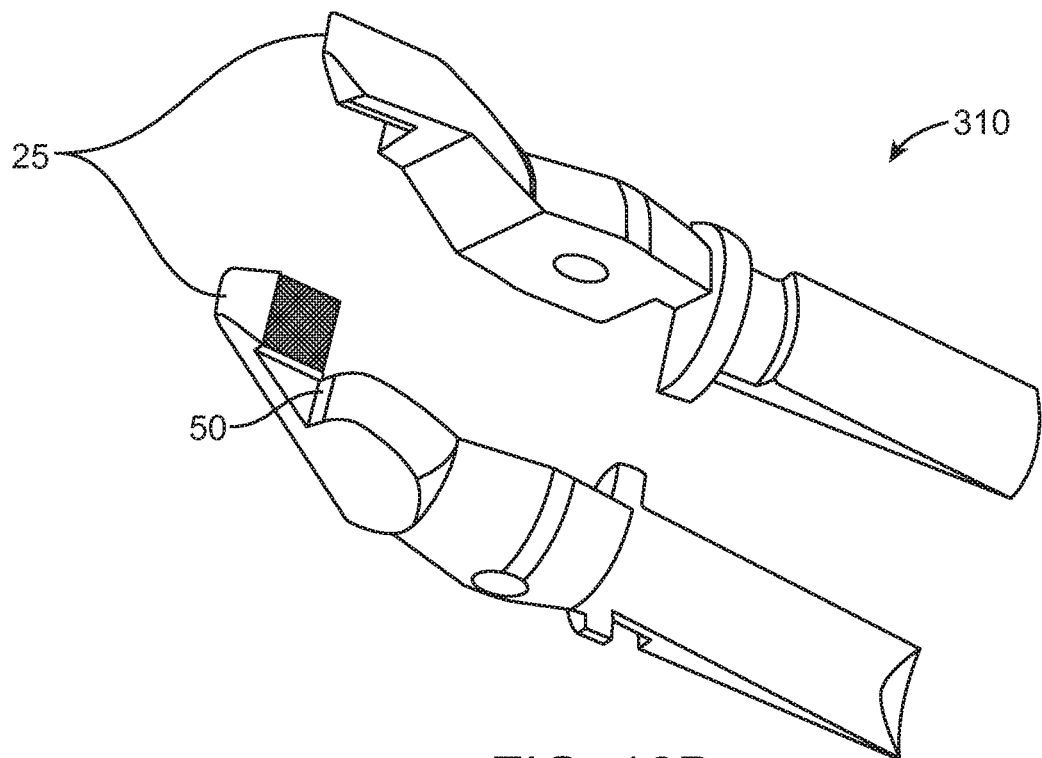
Figure 16C:
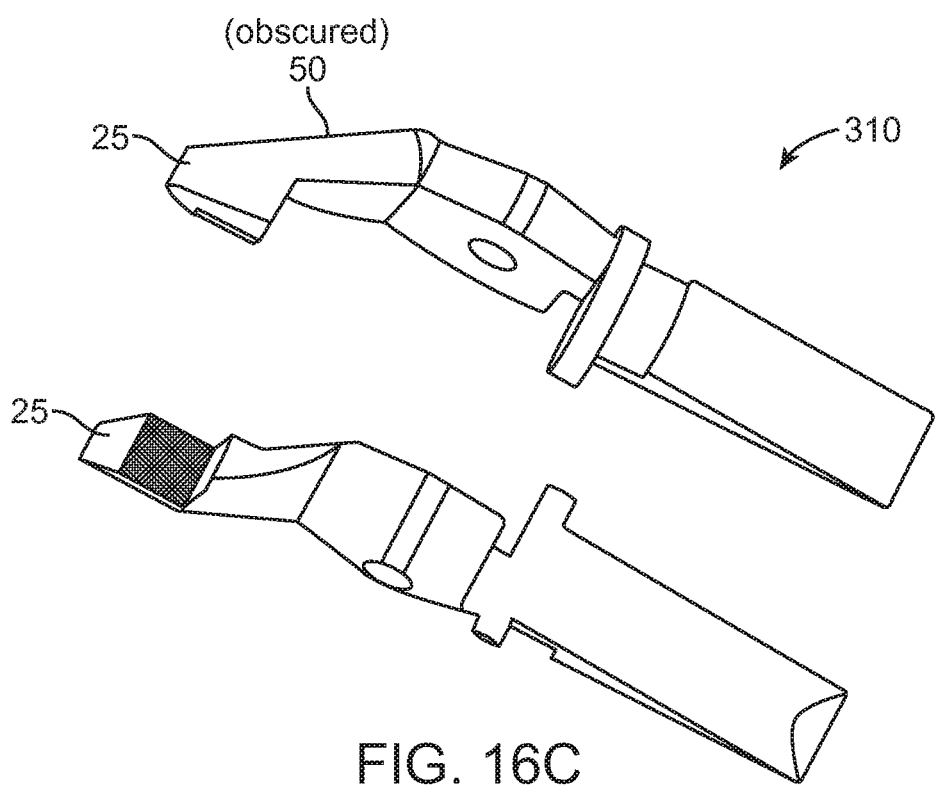
Figure 17:
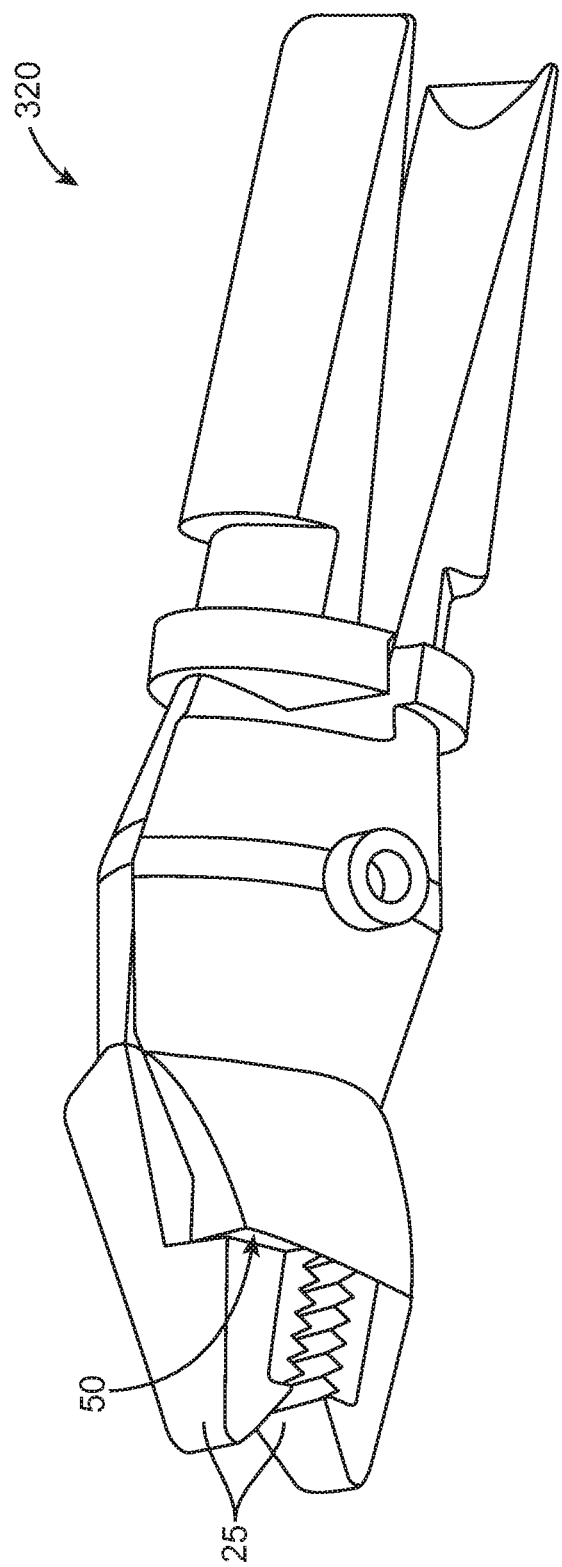
FIG. 17 is a detail view of an alternative clamp embodiment having angled jaws.

In another aspect, a device in accordance with many embodiments may include clamps having angled or curved jaw members 25 and one or more needle contacting surfaces 50, such as those shown in device 300 of FIGS. 15A-15D, device 310 of FIGS. 16A-C, and device 320 of FIG. 17. As shown in exemplary device 300 in FIG. 15C, the needle contacting surface 50 may comprise a portion of a curved surface of jaw 25. A detail of a similar contacting surface 50 is also illustrated in detail in the exemplary device 310 in FIG. 16B.

While exemplary embodiments of the invention have been described in detail, by way of example and for clarity of understanding, a variety of modifications, changes, and adaptations will be obvious to those of skill in the art. For example, along with the exemplary clamp and jaw configuration and mechanisms described herein, still further needle contacting surfaces, designs, and actuation mechanisms may be provided, yet still remain within the scope of the present invention. Hence, the scope of the present invention is limited solely by the appended claims.

What is claimed is:

1. A suturing device comprising:
   a drive unit;
   a clamp extending from the drive unit and having a first jaw and a second jaw, the first jaw and the second jaw being configured to pivot relative to each other between an open configuration and a closed configuration; and
   an actuation handle connected to the drive unit that causes the clamp to move between the closed configuration and open configuration, wherein
   the first jaw includes a first grasping portion and a first offset portion,
   the first offset portion includes a first contact surface extending laterally outward in a first direction away from the first grasping portion and extending away from the first grasping portion in a second direction towards the second jaw,
   the second jaw includes a second grasping portion and a second offset portion,
   the second offset portion includes a second contact surface extending laterally outward in a third direction away from the second grasping portion and opposite the first direction and extending away from the second grasping portion toward the first jaw in a fourth direction that is opposite the second direction,
   in the open configuration the first grasping portion and the second grasping portion are spaced apart,
   in the closed configuration the first grasping portion and the second grasping portion are spaced in close proximity for grasping between the first grasping portion and the second grasping portion, and
   in the closed configuration, a portion of the first jaw and a portion of the second contact surface directly face each other, and a portion of the second jaw and a portion of the first contact surface directly face each other.

2. The suturing device of claim 1, wherein the first contact surface extends away from the first grasping portion towards the second grasping portion.

3. The suturing device of claim 1, wherein the first contact surface and the second contact surface are co-planar in the closed configuration.

4. The suturing device of claim 1, wherein the first grasping portion is bounded by a first plane and the second grasping portion is bounded by a second plane, and the first plane and the second plane are substantially parallel in the closed configuration.

5. The suturing device of claim 4, wherein the first plane and the second plane in the closed configuration are substantially perpendicular to the first contact surface.

6. The suturing device of claim 1, wherein the first offset portion extends a distance in the first direction at least 1/8th that of the width of the first grasping portion.

7. The suturing device of claim 6, wherein the distance is at least half the width of the first grasping portion.

8. The suturing device of claim 6, wherein the distance is between half and twice the width of the first grasping portion.

9. The suturing device of claim 1, wherein the drive unit comprises two actuated members that pivot along an intermediate portion of each member to move the first grasping portion and the second grasping portion between the open configuration and closed configuration.

10. The suturing device of claim 1 further comprising:
    a second clamp extending from the drive unit and having a third jaw and a fourth jaw, the third jaw and the fourth jaw being configured to pivot relative to each other between an open configuration and a closed configuration.

11. The suturing device of claim 10, wherein the drive unit is configured to alternate between the clamp and the second clamp, wherein a first actuation of the drive unit alternates one of the clamp and the second clamp from the open configuration to the closed configuration.

12. The suturing device of claim 11, wherein a second actuation of the drive unit alternates the other of the clamp and the second clamp from the closed configuration to the open configuration.

13. The suturing device of claim 10, wherein
    the third jaw includes a third grasping portion and a third offset portion,
    the third offset portion includes a third contact surface extending laterally outward in a third direction away from the third grasping portion and extending away from the third grasping portion towards the fourth jaw,
    the fourth jaw includes a fourth grasping portion and a fourth offset portion, the fourth offset portion includes a fourth contact surface extending laterally outward in a fourth direction away from the fourth grasping portion and opposite the third direction and extending away from the fourth grasping portion toward the third jaw,
    in the open configuration the third grasping portion and the fourth grasping portion are spaced apart,
    in the closed configuration the third grasping portion and the fourth grasping portion are spaced in close proximity for grasping between the third grasping portion and the fourth grasping portion and against at least one of the third contact surface and the fourth contact surface.

14. The suturing device of claim 1, wherein at least one of the first grasping portion and the second grasping portion comprises a ridged surface having a plurality of ridges extending toward the other one of the first grasping portion and the second grasping portion.

15. The suturing device of claim 14, wherein each of the ridges of the plurality is dimensioned to correspond to a needle geometry.

16. The suturing device of claim 15, wherein the ridges comprise triangular ridges.

17. The suturing device of claim 16, wherein the triangular ridges are dimensioned so as to fittingly receive an apex of a triangular cross-section of a triangular surgical needle so as to inhibit rotational movement of the triangular surgical needle about the triangular cross-section.

18. The suturing device of claim 1, wherein the first grasping portion extends laterally beyond the first contact surface in the third direction, and the second grasping portion extends laterally beyond the second contact surface in the first direction.

19. The suturing device of claim 1, wherein the first and third directions are perpendicular to the second and fourth directions.

* * * * *